United States Patent
Sakamoto et al.

(10) Patent No.: US 9,776,954 B2
(45) Date of Patent: Oct. 3, 2017

(54) POLYMERIZABLE COMPOUND, POLYMERIZABLE COMPOSITION, POLYMER, AND OPTICALLY ANISOTROPIC SUBSTANCE

(71) Applicant: ZEON CORPORATION, Tokyo (JP)

(72) Inventors: Kei Sakamoto, Tokyo (JP); Satoshi Kiriki, Tokyo (JP); Kumi Okuyama, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 337 days.

(21) Appl. No.: 14/436,526

(22) PCT Filed: Oct. 16, 2013

(86) PCT No.: PCT/JP2013/078099
§ 371 (c)(1),
(2) Date: Apr. 17, 2015

(87) PCT Pub. No.: WO2014/061709
PCT Pub. Date: Apr. 24, 2014

(65) Prior Publication Data
US 2015/0274647 A1    Oct. 1, 2015

(30) Foreign Application Priority Data
Oct. 19, 2012 (JP) ................................ 2012-232314

(51) Int. Cl.
| C08F 26/00 | (2006.01) |
| C08F 126/00 | (2006.01) |
| C07D 241/02 | (2006.01) |
| C07C 69/52 | (2006.01) |
| C07C 251/86 | (2006.01) |
| C07D 295/22 | (2006.01) |
| C08F 222/10 | (2006.01) |
| G02B 5/30 | (2006.01) |
| C07C 251/88 | (2006.01) |
| C07D 295/30 | (2006.01) |
| C08F 22/22 | (2006.01) |
| G02B 1/04 | (2006.01) |
| G02F 1/13363 | (2006.01) |

(52) U.S. Cl.
CPC .......... *C07C 251/86* (2013.01); *C07C 251/88* (2013.01); *C07D 295/22* (2013.01);
(Continued)

(58) Field of Classification Search
CPC .. C08F 222/1006; C08F 22/22; C07C 251/88; C07C 251/86; B02B 5/3083;
(Continued)

(56) References Cited

U.S. PATENT DOCUMENTS

| 5,567,349 A | 10/1996 | Kelly et al. |
| 6,139,771 A | 10/2000 | Walba et al. |

(Continued)

FOREIGN PATENT DOCUMENTS

| JP | 10-068816 A | 3/1998 |
| JP | 10-090521 A | 4/1998 |

(Continued)

OTHER PUBLICATIONS

International Preliminary Report on Patentability and Written Opinion of the International Searching Authority (Forms PCT/IB/373, PCT/ISA/237, and PCT/IB/326) for International Application No. PCT/JP2013/078099, issued Apr. 21, 2015, with an English translation.

(Continued)

*Primary Examiner* — William Cheung
(74) *Attorney, Agent, or Firm* — Birch, Stewart, Kolasch & Birch, LLP

(57) ABSTRACT

The present invention relates to: a polymerizable compound represented by a formula (I); a polymerizable composition comprising the polymerizable compound and an initiator; a polymer obtained by polymerizing the polymerizable compound or the polymerizable composition; and an optically anisotropic article comprising the polymer [in the formula, $Y^1$ to $Y^8$ are a chemical single bond, —O—, —O—C(=O)—, —C(=O)—O—, or the like; $G^1$ and $G^2$ are a divalent aliphatic group having 1 to 20 carbon atoms, or the like; $Z^1$ and $Z^2$ are an alkenyl group having 2 to 10 carbon atoms, or the like; $A^1$ is a tetravalent aromatic group, or the like; $A^2$ and $A^3$ are a divalent alicyclic hydrocarbon group having 3 to 30 carbon atoms, or the like; $A^4$ and $A^5$ are a divalent aromatic group having 4 to 30 carbon atoms, or the like; $A^{x1}$ and $A^{x2}$ are an organic group having 2 to 30 carbon atoms that includes an aromatic ring, or the like; $A^{y1}$ and $A^{y2}$ are a hydrogen atom, an alkyl group having 1 to 6 carbon atoms, or the like; $Q^1$ and $Q^2$ are a hydrogen atom, an alkyl group having 1 to 6 carbon atoms, or the like; and m and n are 0 or 1]. According to the present invention, a polymerizable compound, a polymerizable composition, and a polymer that have a practical low melting point, exhibit excellent solubility in a general-purpose solvent, can be produced at low cost, and can produce an optical film that achieves uniform conversion of polarized light over a wide wavelength band, and also provide an optically anisotropic article.

(I)

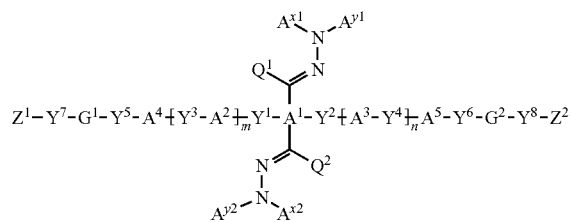

20 Claims, No Drawings

(52) U.S. Cl.
CPC ............ *C07D 295/30* (2013.01); *C08F 22/22* (2013.01); *C08F 222/1006* (2013.01); *G02B 1/04* (2013.01); *G02B 5/3016* (2013.01); *G02B 5/3083* (2013.01); *G02F 2001/133637* (2013.01); *G02F 2001/133638* (2013.01)

(58) Field of Classification Search
CPC ....... B02B 5/3016; B02B 1/04; C07D 295/22; C07D 295/30; G02F 2001/133638; G02F 2001/133637
USPC .................. 526/263, 312; 544/357; 560/221
See application file for complete search history.

(56) References Cited

U.S. PATENT DOCUMENTS

| | | | |
|---|---|---|---|
| 6,203,724 | B1 | 3/2001 | Reiffenrath et al. |
| 6,565,974 | B1 | 5/2003 | Uchiyama et al. |
| 8,454,857 | B2 * | 6/2013 | Sakamoto ............ C07C 251/88 252/299.01 |
| 2002/0159005 | A1 | 10/2002 | Arakawa et al. |
| 2003/0102458 | A1 | 6/2003 | Nishikawa et al. |
| 2007/0176145 | A1 | 8/2007 | Nishikawa et al. |
| 2007/0298191 | A1 | 12/2007 | Yamahara et al. |
| 2009/0072194 | A1 | 3/2009 | Yamahara et al. |
| 2009/0189120 | A1 | 7/2009 | Takeuchi |
| 2010/0201920 | A1 | 8/2010 | Adlem et al. |
| 2010/0258764 | A1 | 10/2010 | Sakamoto et al. |
| 2010/0301271 | A1 | 12/2010 | Adlem et al. |
| 2014/0107247 | A1 | 4/2014 | Sakamoto et al. |
| 2014/0142266 | A1 | 5/2014 | Sakamoto et al. |
| 2014/0235857 | A1 | 8/2014 | Sakamoto et al. |

FOREIGN PATENT DOCUMENTS

| | | |
|---|---|---|
| JP | 11-052131 A | 2/1999 |
| JP | 2001-004837 A | 1/2001 |
| JP | 2002-267838 A | 9/2002 |
| JP | 2005-208414 A | 8/2005 |
| JP | 2005-208415 A | 8/2005 |
| JP | 2005-208416 A | 8/2005 |
| JP | 2008-291218 A | 12/2008 |
| JP | 2009-149754 A | 7/2009 |
| JP | 2010-031223 A | 2/2010 |
| JP | 2011-006360 A | 1/2011 |
| JP | 2011-006361 A | 1/2011 |
| JP | 2011-042606 A | 3/2011 |
| WO | WO 2012/141245 A1 | 10/2012 |
| WO | WO 2012/147904 A1 | 11/2012 |
| WO | WO 2013/018526 A1 | 2/2013 |
| WO | WO 2013/046781 A1 | 4/2013 |

OTHER PUBLICATIONS

International Search Report issued in PCT/JP2013/078099, mailed on Nov. 19, 2013.
Extended European Search Report dated Feb. 22, 2016, issued in European Patent Application 13847704.7.
Office Action dated Jan. 24, 2017, issued in European Patent Application No. 13847704.7.

* cited by examiner

POLYMERIZABLE COMPOUND, POLYMERIZABLE COMPOSITION, POLYMER, AND OPTICALLY ANISOTROPIC SUBSTANCE

This application is a U.S. national stage application under 35 U.S.C. §371 of International Patent Application No. PCT/JP2013/078099 filed on Oct. 16, 2013, which claims the benefit of foreign priority to Japanese Patent Application No. JP 2012-232314 filed on Oct. 19, 2012.

TECHNICAL FIELD

The present invention relates to a polymerizable compound, a polymerizable composition, and a polymer that may produce an optical film that achieves uniform conversion of polarized light over a wide wavelength band, and also relates to an optically anisotropic article.

A flat panel display (FPD) that utilizes an optical film (e.g., polarizer and retardation film) can achieve high-resolution display, and has been widely used as a display device that exhibits excellent performance.

Examples of the retardation film include a quarter-wave plate that converts linearly polarized light into circularly polarized light, a half-wave plate that changes the plane of vibration of linearly polarized light by 90°, and the like. These retardation films can achieve accurate conversion of specific monochromatic light so that ¼λ, or ½λ, retardation occurs.

However, known retardation films have a problem in that polarized light that passes through is converted into colored polarized light. Specifically, since a material that forms the retardation film has wavelength dispersion with respect to retardation, and a polarization state distribution corresponding to each wavelength occurs with respect to white light that includes different light beams in the visible region, it is impossible to achieve accurate 1/4λ, or ½λ, retardation over the entire wavelength band.

In order to solve the above problem, various wideband retardation films that can achieve uniform retardation for light over a wide wavelength band (i.e., retardation films having reverse wavelength dispersion) have been studied (see Patent Documents 1 to 6).

It has been desired to reduce the thickness of the flat panel display as much as possible along with an improvement in performance and widespread use of mobile information terminals (e.g., mobile personal computer and mobile phone). Therefore, a reduction in thickness of the retardation film has also been desired.

It has been considered that it is most effective to produce a retardation film by applying a polymerizable composition that includes a low-molecular-weight polymerizable compound to a film substrate in order to reduce the thickness of the retardation film. Various low-molecular-weight polymerizable compounds having excellent wavelength dispersion, and various polymerizable compositions using such polymerizable compounds have been developed (see Patent Documents 7 to 24).

However, the low-molecular-weight polymerizable compounds or the polymerizable compositions disclosed in Patent Documents 7 to 24 have a number of problems in that reverse wavelength dispersion may be insufficient, or it may be difficult to apply the low-molecular-weight polymerizable compounds or the polymerizable compositions to a film due to a high melting point that is not suitable for an industrial process, or the temperature range in which liquid crystallinity is obtained may be very narrow, or solubility in a solvent generally used for an industrial process may be low. Moreover, since the above low-molecular-weight polymerizable compounds and the like are synthesized by performing a plurality of steps using a synthesis method that utilizes an expensive reagent, the production cost increases.

RELATED-ART DOCUMENT

Patent Document

Patent Document 1: JP-A-10-68816
Patent Document 2: JP-A-10-90521
Patent Document 3: JP-A-11-52131
Patent Document 4: JP-A-2000-284126 (US20020159005A1)
Patent Document 5: JP-A-2001-4837
Patent Document 6: WO2000/026705
Patent Document 7: JP-A-2002-267838
Patent Document 8: JP-A-2003-160540 (US20030102458A1)
Patent Document 9: JP-A-2005-208414
Patent Document 10: JP-A-2005-208415
Patent Document 11: JP-A-2005-208416
Patent Document 12: JP-A-2005-289980 (US20070176145A1)
Patent Document 13: JP-A-2006-330710 (US20090072194A1)
Patent Document 14: JP-A-2009-179563 (US20090189120A1)
Patent Document 15: JP-A-2010-31223
Patent Document 16: JP-A-2011-6360
Patent Document 17: JP-A-2011-6361
Patent Document 18: JP-A-2011-42606
Patent Document 19: JP-T-2010-537954 (US20100201920A1)
Patent Document 20: JP-T-2010-537955 (US20100301271A1)
Patent Document 21: WO2006/052001 (US20070298191A1)
Patent Document 22: U.S. Pat. No. 6,139,771
Patent Document 23: U.S. Pat. No. 6,203,724
Patent Document 24: U.S. Pat. No. 5,567,349

SUMMARY OF THE INVENTION

Technical Problem

The invention was conceived in view of the above situation. An object of the invention is to provide a polymerizable compound, a polymerizable composition, and a polymer that have a practical low melting point, exhibit excellent solubility in a general-purpose solvent, can be produced at low cost, and can produce an optical film that achieves uniform conversion of polarized light over a wide wavelength band, and also provide an optically anisotropic article.

Solution to Problem

The inventors of the invention conducted extensive studies in order to solve the above problem. As a result, the inventors found that an optical film that achieves uniform conversion of polarized light over a wide wavelength band, and exhibits satisfactory performance, can be produced at low cost by utilizing an optically anisotropic article produced using a polymer that is obtained by polymerizing a polymerizable compound represented by the following formula (I), or a polymerizable composition that includes the polymerizable compound and an initiator. This finding has led to the completion of the invention.

Several aspects of the invention provide the following polymerizable compound (see (1) to (9)), polymerizable composition (see (10) and (11)), polymer (see (12) and (13)), and optically anisotropic article (see (14)).

(1) A polymerizable compound represented by the following formula (I),

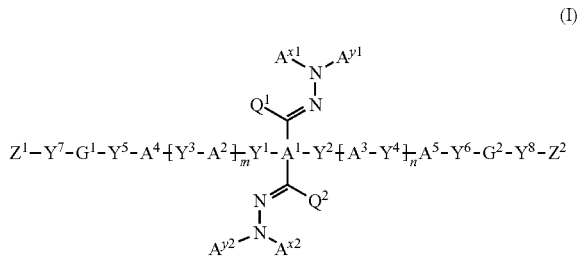

wherein $Y^1$ to $Y^8$ are independently a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—,
$R^1$ is a hydrogen atom or an alkyl group having 1 to 6 carbon atoms,
$G^1$ and $G^2$ are independently a substituted or unsubstituted divalent aliphatic group having 1 to 20 carbon atoms that optionally includes —O—, —S—, —O—C(=O)—, —C(=O)—O—, —O—C(=O)—O—, —NR$^2$—C(=O)—, —C(=O)—NR$^2$—, —NR$^2$—, or —C(=O)—, provided that a case where the aliphatic group includes two or more contiguous —O— or —S— is excluded, $R^2$ is a hydrogen atom or an alkyl group having 1 to 6 carbon atoms,
$Z^1$ and $Z^2$ are independently an alkenyl group having 2 to 10 carbon atoms that is substituted with a halogen atom, or unsubstituted,
$A^1$ is a substituted or unsubstituted tetravalent aromatic group having 4 to 30 carbon atoms,
$A^2$ and $A^3$ are independently a substituted or unsubstituted divalent alicyclic hydrocarbon group having 3 to 30 carbon atoms,
$A^4$ and $A^5$ are independently a substituted or unsubstituted divalent aromatic group having 4 to 30 carbon atoms,
$A^{x1}$ and $A^{x2}$ are independently an organic group having 2 to 30 carbon atoms that includes at least one ring selected from the group consisting of a hydrocarbon ring and a heterocyclic ring,
$A^{y1}$ and $A^{y2}$ are independently a hydrogen atom, a substituted or unsubstituted alkyl group having 1 to 6 carbon atoms, or an organic group having 2 to 30 carbon atoms that includes at least one ring selected from the group consisting of a hydrocarbon ring and a heterocyclic ring,
provided that the ring included in $A^{x1}$, the ring included in $A^{x2}$, the ring optionally included in $A^{y1}$, and the ring optionally included in $A^{y2}$ are either substituted or unsubstituted,
$A^{x1}$ and $A^{y1}$ are optionally bonded to each other to form a ring, and $A^{x2}$ and $A^{y2}$ are optionally bonded to each other to form a ring,
$Q^1$ and $Q^2$ are independently a hydrogen atom, or a substituted or unsubstituted alkyl group having 1 to 6 carbon atoms, and
m and n are independently 0 or 1.

(2) The polymerizable compound according to (1), wherein the ring included in $A^{x1}$, the ring included in $A^{x2}$, the ring optionally included in $A^{y1}$, and the ring optionally included in $A^{y2}$ are an aromatic ring.

(3) The polymerizable compound according to (1), wherein the total number of aromatic ring π electrons included in $A^{x1}$ and $A^{y1}$ is 24 or less, and the total number of aromatic ring π electrons included in $A^{x2}$ and $A^{y2}$ is 24 or less.

(4) The polymerizable compound according to (1), wherein the ring that is optionally formed by $A^{x1}$ and $A^{y1}$, and the ring that is optionally formed by $A^{x2}$ and $A^{y2}$, are a nitrogen-containing heterocyclic ring represented by the following formula (II),

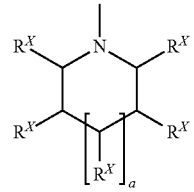

wherein $R^x$ are a hydrogen atom, a halogen atom, an alkyl group having 1 to 6 carbon atoms, a cyano group, a nitro group, an alkylsulfinyl group having 1 to 6 carbon atoms, an alkylsulfonyl group having 1 to 6 carbon atoms, a fluoroalkyl group having 1 to 6 carbon atoms, or an alkoxy group having 1 to 6 carbon atoms, provided that $R^x$ are either identical or different, an arbitrary C—$R^x$ linkage that forms the ring is optionally substituted with N—$R^3$ ($R^3$ is a hydrogen atom or an alkyl group having 1 to 6 carbon atoms) or —O—, and the ring optionally includes an unsaturated bond, a is an integer from 0 to 2, and "-" is the bonding position.

(5) The polymerizable compound according to (1), wherein $A^1$ is a substituted or unsubstituted tetravalent benzene ring group, or a substituted or unsubstituted tetravalent naphthalene ring group, and $A^4$ and $A^5$ are independently a substituted or unsubstituted phenylene group, or a substituted or unsubstituted naphthylene group.

(6) The polymerizable compound according to (1), wherein $Y^1$ to $Y^8$ are independently a chemical single bond, —O—, —O—C(=O)—, —C(=O)—O—, or —O—C(=O)—O—.

(7) The polymerizable compound according to (1), wherein $Z^1$ and $Z^2$ are independently CH$_2$=CH—, CH$_2$=C(CH$_3$)—, or CH$_2$=C(Cl)—.

(8) The polymerizable compound according to (1), wherein $G^1$ and $G^2$ are independently a substituted or unsubstituted divalent aliphatic group having 1 to 12 carbon atoms that optionally includes —O—, —O—C(=O)—, —C(=O)—O—, or —C(=O)—, provided that a case where the aliphatic group includes two or more contiguous —O— is excluded.

(9) The polymerizable compound according to (1), wherein $Y^1$ to $Y^8$ are independently a chemical single bond, —O—, —O—C(=O)—, —C(=O)—O—, or —O—C(=O)—O—, $Z^1$ to $Z^3$ are independently CH$_2$=CH—, CH$_2$=C(CH$_3$)—, or CH$_2$=C(Cl)—, and $G^1$ and $G^2$ are independently a divalent alkylene group having 1 to 12 carbon atoms.

(10) A polymerizable composition including at least one type of the polymerizable compound according to any one of (1) to (9).

(11) A polymerizable composition including the polymerizable compound according to any one of (1) to (9), and an initiator.
(12) A polymer obtained by polymerizing the polymerizable compound according to any one of (1) to (9), or the polymerizable composition according to (10) or (11).
(13) The polymer according to (12), the polymer being a liquid crystalline polymer.
(14) An optically anisotropic article including the polymer according to (13).

Advantageous Effects of the Invention

The polymerizable compound, the polymerizable composition, and the polymer according to the aspects of the invention make it possible to inexpensively obtain an optically anisotropic article that achieves uniform conversion of polarized light over a wide wavelength band, and exhibits satisfactory performance.

Since the optically anisotropic article according to one aspect of the invention is produced using the polymer according to one aspect of the invention, the optically anisotropic article can be produced at low cost, achieves uniform conversion of polarized light over a wide wavelength band, and exhibits satisfactory performance.

For example, an antireflective film may be produced by combining the film-shaped optically anisotropic article according to one aspect of the invention with a polarizer. The antireflective film may suitably be used to prevent reflection from a touch panel, an organic electroluminescent device, and the like.

DESCRIPTION OF EMBODIMENTS

A polymerizable compound, a polymerizable composition, a polymer, and an optically anisotropic article according to several exemplary embodiments of the invention are described in detail below.
1) Polymerizable Compound A polymerizable compound according to one embodiment of the invention is a compound represented by the formula (I).

$Y^1$ to $Y^8$ in the formula (1) are independently a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—.

$R^1$ is a hydrogen atom or an alkyl group having 1 to 6 carbon atoms.

Examples of the alkyl group having 1 to 6 carbon atoms represented by $R^1$ include a methyl group, an ethyl group, an n-propyl group, an isopropyl group, an n-butyl group, a sec-butyl group, a t-butyl group, an n-pentyl group, an n-hexyl group, and the like.

$R^1$ is preferably a hydrogen atom or an alkyl group having 1 to 4 carbon atoms.

It is preferable that $Y^1$ to $Y^8$ be independently a chemical single bond, —O—, —O—C(=O)—, —C(=O)—O—, or —O—C(=O)—O—.

$G^1$ and $G^2$ are independently a substituted or unsubstituted divalent aliphatic group having 1 to 20 carbon atoms.

Examples of the divalent aliphatic group having 1 to 20 carbon atoms include a divalent aliphatic group having a linear structure; a divalent aliphatic group having an alicyclic structure such as a saturated cyclic hydrocarbon (cycloalkane) structure or an unsaturated cyclic hydrocarbon (cycloolefin) structure; and the like.

Examples of a substituent that may substitute the divalent aliphatic group represented by $G^1$ and $G^2$ include a halogen atom such as a fluorine atom, a chlorine atom, a bromine atom, and an iodine atom; an alkoxy group having 1 to 6 carbon atoms, such as a methoxy group, an ethoxy group, an n-propoxy group, an isopropoxy group, an n-butoxy group, a sec-butoxy group, a t-butoxy group, an n-pentyloxy group, and an n-hexyloxy group; and the like. Among these, a fluorine atom, a methoxy group, and an ethoxy group are preferable.

The aliphatic group optionally includes —O—, —S—, —O—C(=O)—, —C(=O)—O—, —O—C(=O)—O—, —NR$^2$—C(=O)—, —C(=O)—NR$^2$—, —NR$^2$—, or —C(=O)— (provided that a case where the aliphatic group includes two or more contiguous —O— or —S— is excluded). $R^2$ is a hydrogen atom, or an alkyl group having 1 to 6 carbon atoms similar to that represented by $R^1$, and is preferably a hydrogen atom or a methyl group.

—O—, —O—C(=O)—, —C(=O)—O—, and —C(=O)— are preferable as the group that is optionally included in the aliphatic group.

Specific examples of the aliphatic group that includes the above group include —CH$_2$—CH$_2$—O—CH$_2$—CH$_2$—, —CH$_2$—CH$_2$—S—CH$_2$—CH$_2$—, —CH$_2$—CH$_2$—O—C(=O)—CH$_2$—CH$_2$—, —CH$_2$—CH$_2$—C(=O)—O—CH$_2$—CH$_2$—, —CH$_2$—CH$_2$—C(=O)—O—CH$_2$—, —CH$_2$—O—C(=O)—O—CH$_2$—CH$_2$—, —CH$_2$—CH$_2$—NR$^2$—C(=O)—CH$_2$—CH$_2$—, —CH$_2$—CH$_2$—C(=O)—NR$^2$—CH$_2$—, —CH$_2$—NR$^2$—CH$_2$—CH$_2$—, —CH$_2$—C(=O)—CH$_2$—, and the like.

It is preferable that $G^1$ and $G^2$ be independently a divalent aliphatic group having a linear structure (e.g., an alkylene group having 1 to 20 carbon atoms or an alkenylene group having 2 to 20 carbon atoms), more preferably an alkylene group having 1 to 12 carbon atoms (e.g., methylene group, ethylene group, trimethylene group, propylene group, tetramethylene group, pentamethylene group, hexamethylene group, or octamethylene group), and particularly preferably a tetramethylene group (—(CH$_2$)$_4$—) or a hexamethylene group (—(CH$_2$)$_6$—), in order to ensure that the intended effects of the invention can be more advantageously achieved.

$Z^1$ and $Z^2$ are independently an alkenyl group having 2 to 10 carbon atoms that is substituted with a halogen atom, or unsubstituted.

The number of carbon atoms of the alkenyl group is preferably 2 to 6. Examples of the halogen atom that may substitute the alkenyl group represented by $Z^1$ and $Z^2$ include a fluorine atom, a chlorine atom, a bromine atom, and the like. Among these, a chlorine atom is preferable.

Specific examples of the alkenyl group having 2 to 10 carbon atoms represented by $Z^1$ and $Z^2$ include CH$_2$=CH—, CH$_2$=C(CH$_3$)—, CH$_2$=CH—CH$_2$—, CH$_3$—CH=CH—, CH$_2$=CH—CH$_2$—CH$_2$—, CH$_2$=C(CH$_3$)—CH$_2$—CH$_2$—, (CH$_3$)$_2$C=CH—CH$_2$—, (CH$_3$)$_2$C=CH—CH$_2$—CH$_2$—, CH$_2$=C(Cl)—, CH$_2$=C(CH$_3$)—CH$_2$—, CH$_3$—CH=CH—CH$_2$—, and the like.

It is preferable that $Z^1$ and $Z^2$ be independently CH$_2$=CH—, CH$_2$=C(CH$_3$)—, CH$_2$=C(Cl)—, CH$_2$=CH—CH$_2$—, CH$_2$=C(CH$_3$)—CH$_2$—, or CH$_2$=C(CH$_3$)—CH$_2$—CH$_2$—, more preferably CH$_2$=CH—, CH$_2$=C(CH$_3$)—, or CH$_2$=C(Cl)—, and still more preferably CH$_2$=CH—, in order to more advantageously achieve the intended effects of the invention.

$A^{x1}$ and $A^{x2}$ are an organic group having 2 to 30 carbon atoms that includes at least one ring selected from the group consisting of a hydrocarbon ring and a heterocyclic ring.

The organic group having 2 to 30 carbon atoms represented by $A^{x1}$ and $A^{x2}$ may include a plurality of rings, and may include a hydrocarbon ring and a heterocyclic ring.

Examples of the ring included in $A^{x1}$ and $A^{x2}$ include a saturated hydrocarbon ring such as a cyclohexane ring and a cycloheptane ring; a saturated heterocyclic ring such as a tetrahydrofuran ring, a tetrahydrothiophene ring, a piperidine ring, and a pyrrolidine ring; an aromatic hydrocarbon ring; a heteroaromatic ring; and the like. It is preferable that the ring included in $A^{x1}$ and $A^{x2}$ be an aromatic ring such as an aromatic hydrocarbon ring and a heteroaromatic ring, since the advantageous effects of the invention can be more easily achieved.

The term "aromatic ring" used herein refers to a cyclic structure that exhibits aromaticity in a broad sense according to Huckel's rule (i.e., a cyclic conjugated structure that includes (4n+2) π electrons, and a structure that exhibits aromaticity in which lone pairs of heteroatoms (e.g., sulfur, oxygen, or nitrogen) are involved in the π electron system (e.g., thiophene, furan, and benzothiazole).

Examples of the aromatic hydrocarbon ring include a benzene ring, a naphthalene ring, an anthracene ring, and the like.

Examples of the heteroaromatic ring include a monocyclic heteroaromatic ring such as a pyrrole ring, a furan ring, a thiophene ring, a pyridine ring, a pyridazine ring, a pyrimidine ring, a pyrazine ring, a pyrazole ring, an imidazole ring, an oxazole ring, and a thiazole ring; a fused heteroaromatic ring such as a benzothiazole ring, a benzoxazole ring, a quinoline ring, a phthalazine ring, a benzimidazole ring, a benzopyrazole ring, a benzofuran ring, and a benzothiophene ring; and the like.

Examples of a preferable organic group having 2 to 30 carbon atoms represented by $A^{x1}$ and $A^{x2}$ that includes at least one ring selected from the group consisting of a hydrocarbon ring and a heterocyclic ring include an aromatic hydrocarbon ring group; a heteroaromatic ring group; an alkyl group that includes at least one aromatic ring selected from the group consisting of an aromatic hydrocarbon ring group and a heteroaromatic ring group; an alkenyl group that includes at least one aromatic ring selected from the group consisting of an aromatic hydrocarbon ring group and a heteroaromatic ring group; and an alkynyl group that includes at least one aromatic ring selected from the group consisting of an aromatic hydrocarbon ring group and a heteroaromatic ring group.

Specific examples of the organic group preferable as $A^{x1}$ and $A^{x2}$ are shown below. Note that $A^{x1}$ and $A^{x2}$ are not limited to the following organic groups. "-" in the following formulas is a bond from the ring (hereinafter the same).

(1) Aromatic Hydrocarbon Ring Group

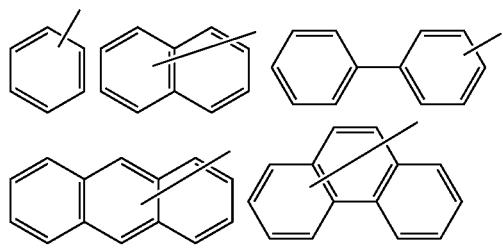

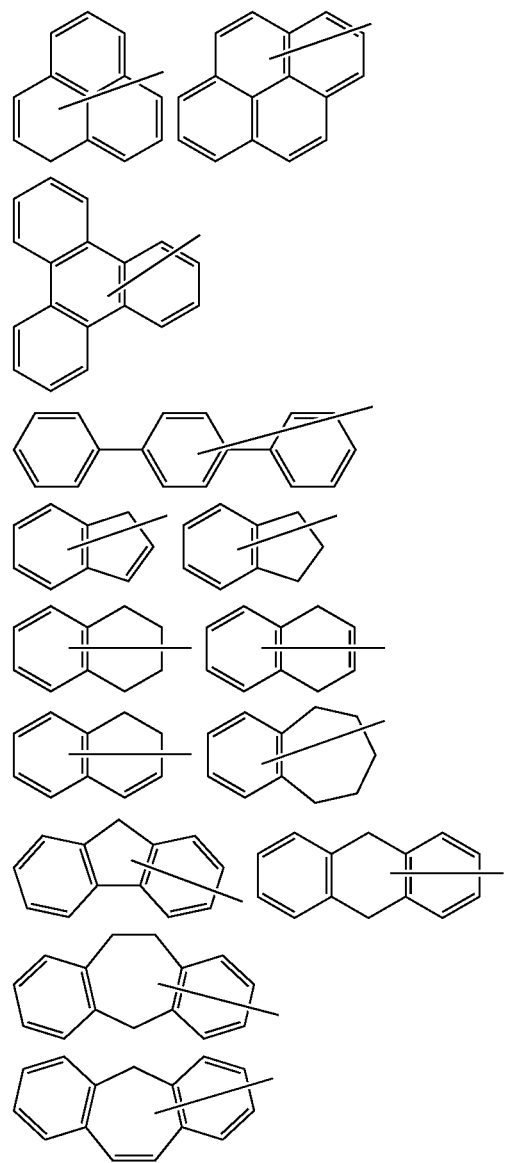

(2) Heteroaromatic Ring Group

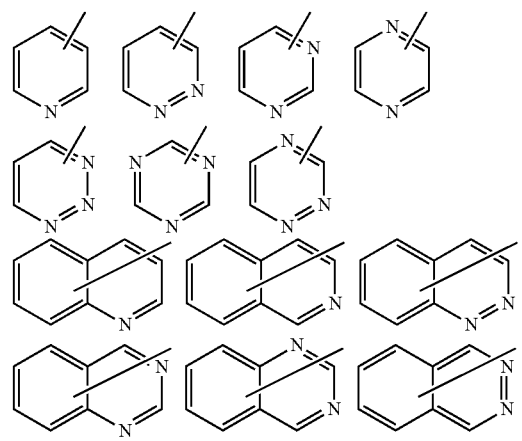

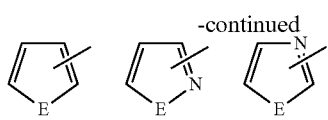

wherein E is NR⁴, an oxygen atom, or a sulfur atom, and R⁴ is a hydrogen atom, or an alkyl group having 1 to 6 carbon atoms (e.g., methyl group, ethyl group, or propyl group).

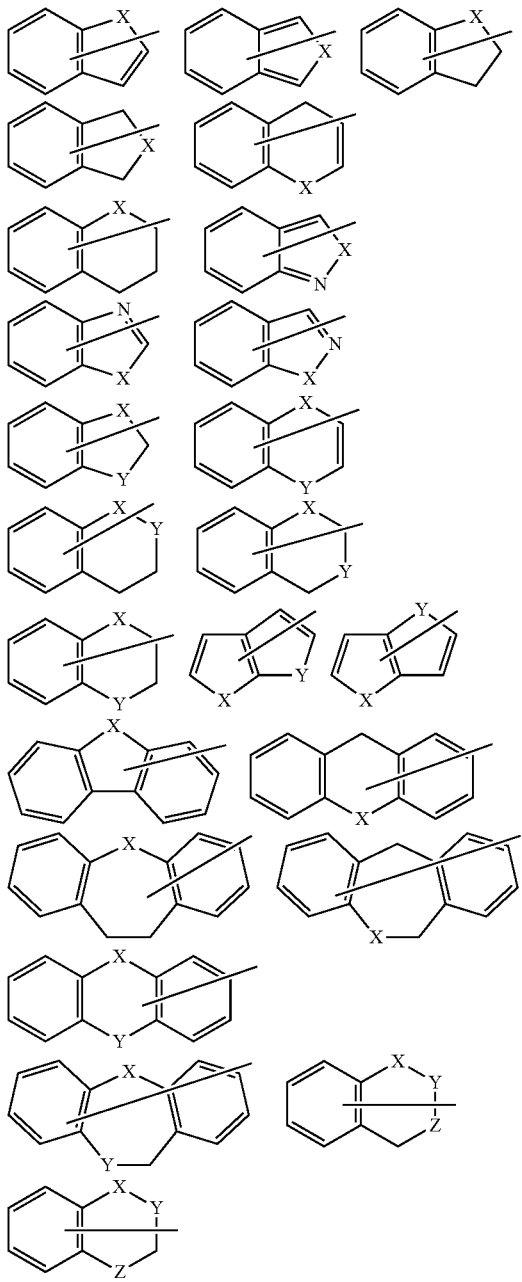

wherein X, Y, and Z are independently NR⁵, an oxygen atom, a sulfur atom, —SO—, or —SO₂— (provided that a case where two or more oxygen atoms, sulfur atoms, —SO—, or —SO₂— are situated at adjacent positions is excluded), and R⁵ is a hydrogen atom, or an alkyl group having 1 to 6 carbon atoms (e.g., methyl group, ethyl group, or propyl group) similar to that represented by R⁴.

(3) Alkyl Group that Includes at Least One Aromatic Ring Selected from the Group Consisting of an Aromatic Hydrocarbon Ring Group and a Heteroaromatic Ring Group

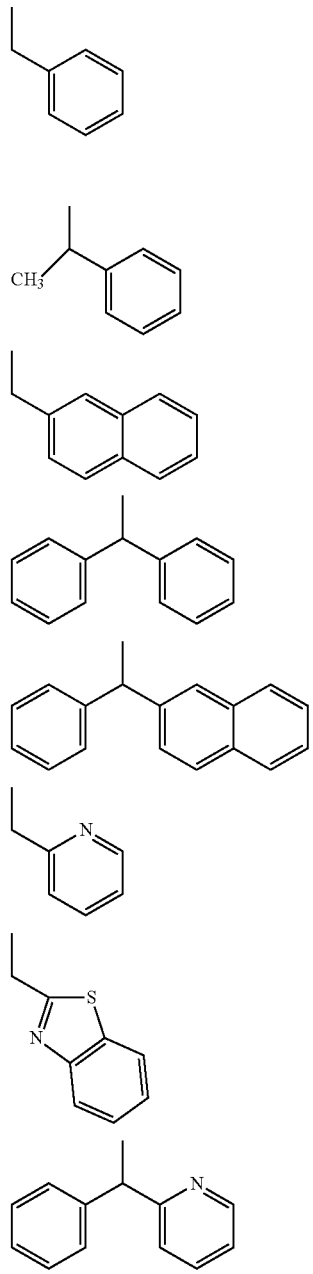

(4) Alkenyl Group that Includes at Least One Aromatic Ring Selected from the Group Consisting of an Aromatic Hydrocarbon Ring Group and a Heteroaromatic Ring Group

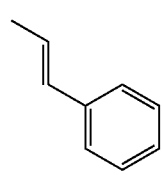

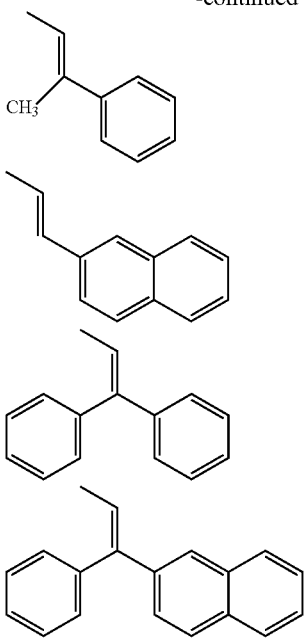

(5) Alkynyl Group that Includes at Least One Aromatic Ring Selected from the Group Consisting of an Aromatic Hydrocarbon Ring Group and a Heteroaromatic Ring Group

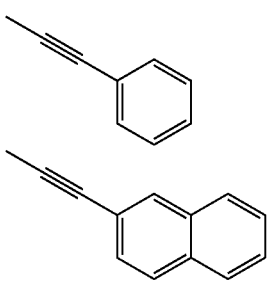

The ring included in $A^{x1}$ and $A^{x2}$ is optionally substituted with a substituent. Examples of the substituent include a halogen atom such as a fluorine atom and a chlorine atom; a cyano group; an alkyl group having 1 to 6 carbon atoms, such as a methyl group, an ethyl group, and a propyl group; an alkenyl group having 2 to 6 carbon atoms, such as a vinyl group and an allyl group; an alkyl halide group having 1 to 6 carbon atoms, such as a trifluoromethyl group; a substituted amino group such as a dimethylamino group; an alkoxy group having 1 to 6 carbon atoms, such as a methoxy group, an ethoxy group, and an isopropoxy group; a nitro group; an aryl group such as a phenyl group and a naphthyl group; —C(=O)—$R^6$; —C(=O)—$OR^6$; —$SO_2R^6$; and the like. Note that $R^6$ is an alkyl group having 1 to 6 carbon atoms (e.g., methyl group or ethyl group), or an aryl group having 6 to 14 carbon atoms (e.g., phenyl group).

The ring included in $A^{x1}$ and $A^{x2}$ may be substituted with a plurality of identical or different substituents, and two adjacent substituents may be bonded to each other to form a ring. The ring formed by two adjacent substituents may be either a monocyclic ring or a fused polycyclic ring.

Note that the number of carbon atoms (i.e., 2 to 30) of the organic group represented by $A^{x1}$ and $A^{x2}$ refers to the total number of carbon atoms of the organic group excluding the number of carbon atoms of a substituent. This also applies to the number of carbon atoms of the organic group represented by $A^{y1}$ and $A^{y2}$.

$A^{y1}$ and $A^{y2}$ are a hydrogen atom, a substituted or unsubstituted alkyl group having 1 to 6 carbon atoms, or an organic group having 2 to 30 carbon atoms that includes at least one ring selected from the group consisting of a hydrocarbon ring and a heterocyclic ring.

Examples of the alkyl group having 1 to 6 carbon atoms represented by $A^{y1}$ and $A^{y2}$ (that is substituted or unsubstituted) include a methyl group, an ethyl group, an n-propyl group, an isopropyl group, an n-butyl group, a sec-butyl group, a t-butyl group, an n-pentyl group, an isopentyl group, a neopentyl group, an n-hexyl group, an isohexyl group, and the like.

Examples of a substituent that may substitute the alkyl group having 1 to 6 carbon atoms include a halogen atom such as a fluorine atom and a chlorine atom; a cyano group; a substituted amino group such as a dimethylamino group; an alkoxy group having 1 to 6 carbon atoms, such as a methoxy group, an ethoxy group, and an isopropoxy group; an alkoxy group having 1 to 6 carbon atoms that is substituted with an alkoxy group having 1 to 6 carbon atoms, such as a methoxymethoxy group and a methoxyethoxy group; a nitro group; an aryl group such as a phenyl group and a naphthyl group; a cycloalkyl group having 3 to 8 carbon atoms, such as a cyclopropyl group, a cyclopentyl group, and a cyclohexyl group; —C(=O)—$R^7$; —C(=O)—$OR^7$; —$SO_2R^7$; a hydroxyl group; and the like. Note that $R^7$ is an alkyl group having 1 to 6 carbon atoms (e.g., methyl group or ethyl group), or an aryl group having 6 to 14 carbon atoms (e.g., phenyl group).

Examples of the organic group having 2 to 30 carbon atoms represented by $A^{y1}$ and $A^{y2}$ that includes at least one ring selected from the group consisting of a hydrocarbon ring and a heterocyclic ring, include those mentioned above in connection with $A^{x1}$ and $A^{x2}$.

The groups respectively represented by the following formulas are preferable as the organic group having 2 to 30 carbon atoms represented by $A^{x1}$, $A^{x2}$, $A^{y1}$, and $A^{y2}$ that includes at least one ring selected from the group consisting of a hydrocarbon ring and a heterocyclic ring.

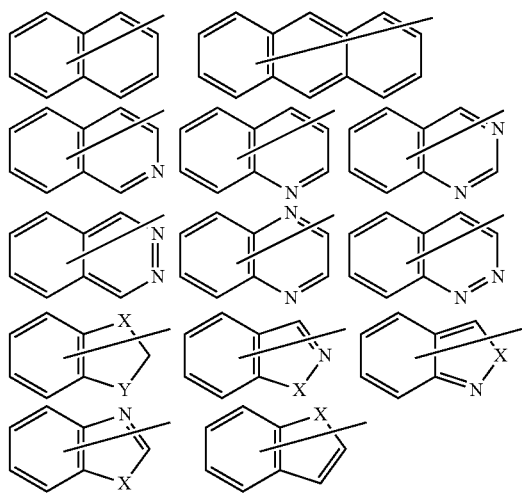

wherein X is the same as defined above.

The groups respectively represented by the following formulas are more preferable as the organic group having 2 to 30 carbon atoms represented by $A^{x1}$, $A^{x2}$, $A^{y1}$, and $A^{y2}$ that includes at least one ring selected from the group consisting of a hydrocarbon ring and a heterocyclic ring.

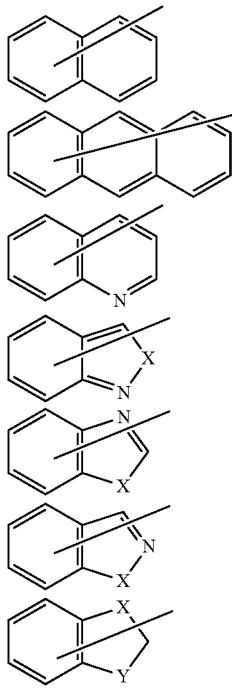

wherein X and Y are the same as defined above.

The groups respectively represented by the following formulas are particularly preferable as the organic group having 2 to 30 carbon atoms represented by $A^{x1}$, $A^{x2}$, $A^{y1}$, and $A^{y2}$ that includes at least one ring selected from the group consisting of a hydrocarbon ring and a heterocyclic ring.

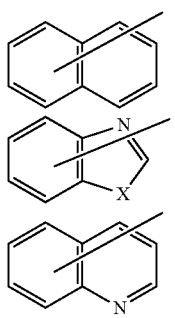

wherein X is the same as defined above.

These groups may be substituted at an arbitrary position with a substituent similar to those mentioned above in connection with the substituent that may substitute the ring included in $A^{x1}$ and the like.

$A^{x1}$ and $A^{y1}$ and/or $A^{x2}$ and $A^{y2}$ are optionally bonded to each other to form a ring. The ring that is optionally formed by $A^{x1}$ and $A^{y1}$ and the ring that is optionally formed by $A^{x2}$ and $A^{y2}$ may be either a monocyclic ring or a fused ring.

A nitrogen-containing heterocyclic ring represented by the following formula (II) is preferable as the ring that is optionally formed by $A^{x1}$ and $A^{y1}$ and the ring that is optionally formed by $A^{x2}$ and $A^{y2}$.

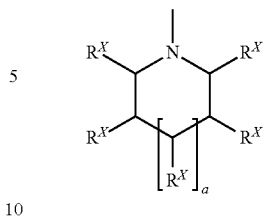

(II)

wherein $R^x$ are a hydrogen atom, a halogen atom (e.g., fluorine atom, chlorine atom, or a bromine atom), an alkyl group having 1 to 6 carbon atoms (e.g., methyl group or ethyl group), a cyano group, a nitro group, an alkylsulfinyl group having 1 to 6 carbon atoms (e.g., methylsulfinyl group or ethylsulfinyl group), an alkylsulfonyl group having 1 to 6 carbon atoms (e.g., methylsulfonyl group or ethylsulfonyl group), a fluoroalkyl group having 1 to 6 carbon atoms (e.g., trifluoromethyl group or pentafluoroethyl group), or an alkoxy group having 1 to 6 carbon atoms (e.g., methoxy group or ethoxy group).

Among these, a hydrogen atom and an alkyl group having 1 to 6 carbon atoms are preferable.

$R^x$ are either identical or different, and adjacent $R^x$ may be bonded to each other to form a ring (e.g., saturated carbon ring or unsaturated carbon ring).

An arbitrary C—$R^x$ linkage that forms the ring is optionally substituted with N—$R^3$ ($R^3$ is a hydrogen atom or an alkyl group having 1 to 6 carbon atoms (e.g., methyl group or ethyl group)) or —O— (provided that a case where two or more contiguous C—$R^x$ linkages are substituted with —O— is excluded). The ring optionally includes an unsaturated bond. When a plurality of C—$R^x$ linkages are substituted with N—$R^3$, a plurality of N—$R^3$ are either identical or different.

a is an integer from 0 to 2, and "-" is the bonding position.

Specific examples of the ring represented by the formula (II) are shown below.

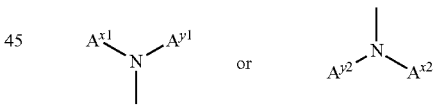

Note that the ring represented by the formula (II) and the rings shown below correspond to the above part in the formula (I).

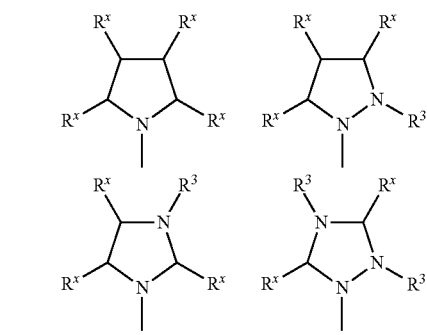

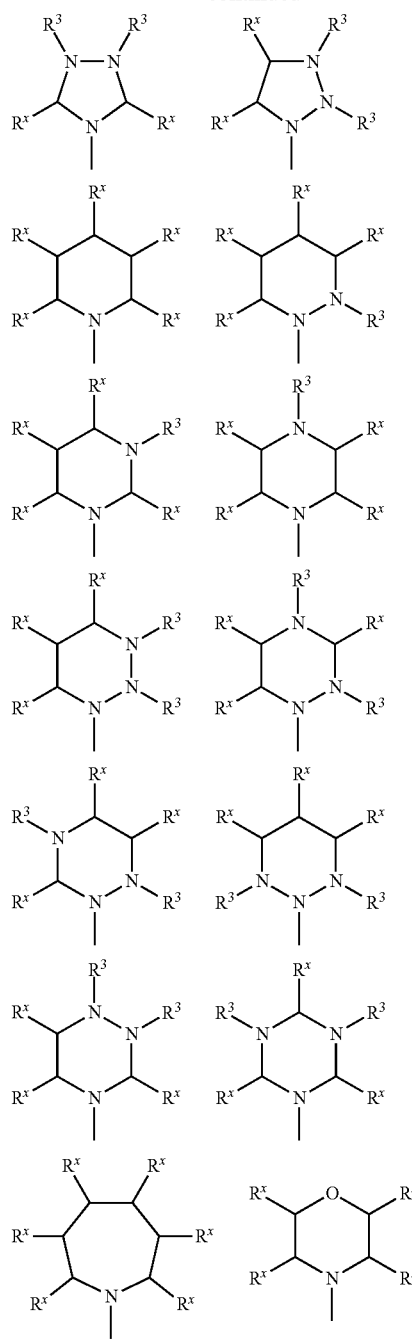
wherein $R^x$ and $R^3$ are the same as defined above.
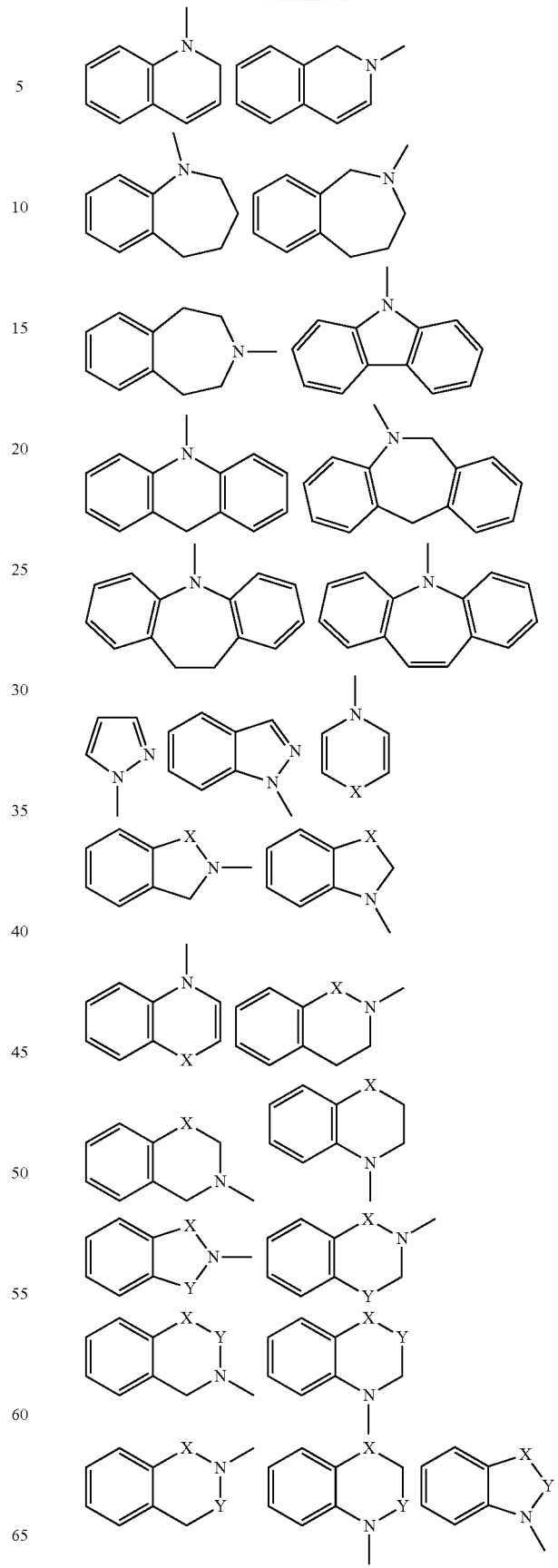

-continued

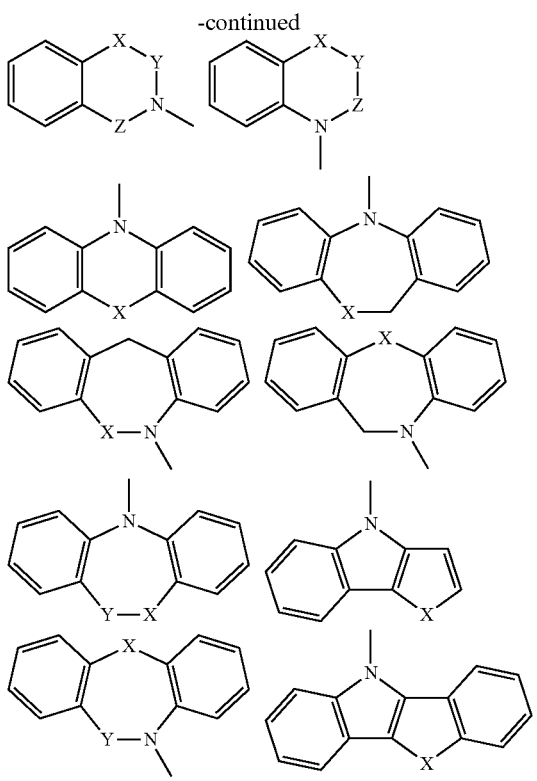

wherein X, Y, and Z are the same as defined above.

These rings may be substituted with a substituent.

Examples of the substituent include a halogen atom, a cyano group, an alkyl group having 1 to 6 carbon atoms, an alkoxy group having 1 to 6 carbon atoms, a nitro group, —C(=O)—R$^8$, —C(=O)—OR$^8$, —SO$_2$R$^4$, and the like. Note that R$^8$ is an alkyl group having 1 to 6 carbon atoms (e.g., methyl group or ethyl group), or an aryl group having 6 to 14 carbon atoms (e.g., phenyl group).

The total number of aromatic ring π electrons included in A$^{x1}$ and A$^{y1}$ and the total number of aromatic ring π electrons included in A$^{x2}$ and A$^{y2}$ are preferably 24 or less, and more preferably 6 to 18, in order to ensure that the intended effects of the invention can be more advantageously achieved.

It is preferable that A$^{x1}$ be an aromatic group having 4 to 30 carbon atoms, and A$^{y1}$ be a hydrogen atom, a cycloalkyl group having 3 to 8 carbon atoms, or an alkyl group having 1 to 20 carbon atoms (that is optionally substituted with a halogen atom, a cyano group, an alkoxy group having 1 to 6 carbon atoms, an alkoxy group having 1 to 6 carbon atoms that is substituted with an alkoxy group having 1 to 6 carbon atoms, or a cycloalkyl group having 3 to 8 carbon atoms), or A$^{x1}$ and A$^{y1}$ be bonded to each other to form the group represented by the formula (II).

It is more preferable that A$^{x1}$ be an aromatic group having 4 to 30 carbon atoms, and A$^{y1}$ be an alkyl group having 1 to 6 carbon atoms, or A$^{x1}$ and A$^{y1}$ be bonded to each other to form the group represented by the formula (II).

Examples of a preferable combination of A$^{x2}$ and A$^{y2}$ include those mentioned above in connection with A$^{x1}$ and A$^{y1}$.

It is preferable that A$^{x1}$ and A$^{x2}$ be identical with each other, and A$^{y1}$ and A$^{y2}$ be identical with each other.

A$^1$ is a substituted or unsubstituted tetravalent aromatic group having 4 to 30 carbon atoms. The tetravalent aromatic group may be a tetravalent carbocyclic aromatic group, or may be a tetravalent heterocyclic aromatic group (heteroaromatic group). It is preferable that the tetravalent aromatic group be a tetravalent carbocyclic aromatic group, more preferably a tetravalent benzene ring group or a tetravalent naphthalene ring group, and still more preferably a tetravalent benzene ring group or a tetravalent naphthalene ring group represented by a formula among the following formulas, in order to ensure that the intended effects of the invention can be more advantageously achieved.

Note that the substituents Y$^1$ and Y$^2$ are also included in the following formulas so that the bonding state can be readily understood (Y$^1$ and Y$^2$ are the same as defined above; hereinafter the same).

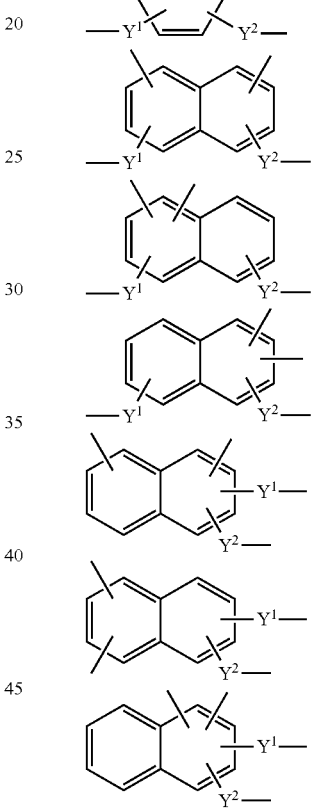

A$^1$ is more preferably a group among the groups respectively represented by the following formulas (A11) to (A19), still more preferably a group among the groups respectively represented by the formulas (A11), (A13), (A15), (A17), and (A18), and particularly preferably the group represented by the formula (A11).

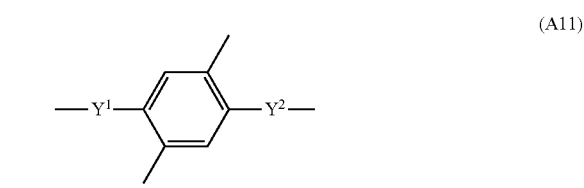

(A11)

-continued

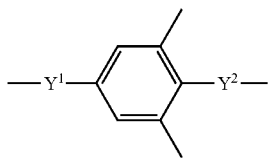
(A12)

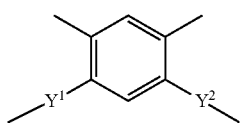
(A13)

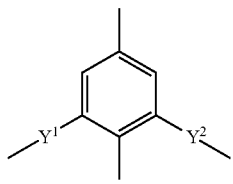
(A14)

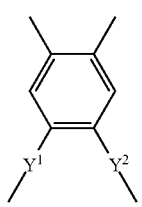
(A15)

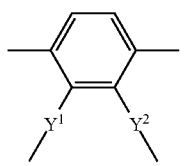
(A16)

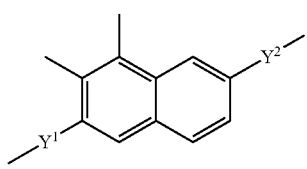
(A17)

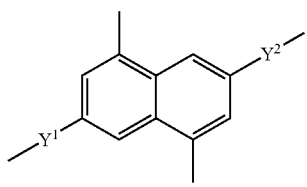
(A18)

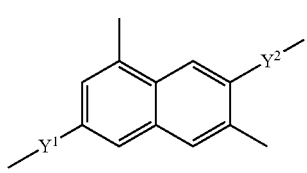
(A19)

Examples of a substituent that may substitute the tetravalent aromatic group having 4 to 30 carbon atoms represented by $A^1$ include those mentioned above in connection with the ring included in $A^{x1}$ and the like. It is preferable that $A^1$ be unsubstituted.

$A^2$ and $A^3$ are independently a substituted or unsubstituted divalent alicyclic hydrocarbon group having 3 to 30 carbon atoms.

Examples of the divalent alicyclic hydrocarbon group having 3 to 30 carbon atoms include a cycloalkanediyl group having 3 to 30 carbon atoms, a divalent fused alicyclic group having 10 to 30 carbon atoms, and the like.

Examples of the cycloalkanediyl group having 3 to 30 carbon atoms include a cyclopropanediyl group; a cyclobutanediyl group such as a cyclobutane-1,2-diyl group and a cyclobutane-1,3-diyl group; a cyclopentanediyl group such as a cyclopentane-1,2-diyl group and a cyclopentane-1,3-diyl group; a cyclohexanediyl group such as a cyclohexane-1,2-diyl group, a cyclohexane-1,3-diyl group, and a cyclohexane-1,4-diyl group; a cycloheptanediyl group such as a cycloheptane-1,2-diyl group, a cycloheptane-1,3-diyl group, and a cycloheptane-1,4-diyl group; a cyclooctanediyl group such as a cyclooctane-1,2-diyl group, a cyclooctane-1,3-diyl group, a cyclooctane-1,4-diyl group, and a cyclooctane-1,5-diyl group; a cyclodecanediyl group such as a cyclodecane-1,2-diyl group, a cyclodecane-1,3-diyl group, a cyclodecane-1,4-diyl group, and a cyclodecane-1,5-diyl group; a cyclododecanediyl group such as a cyclododecane-1,2-diyl group, a cyclododecane-1,3-diyl group, a cyclododecane-1,4-diyl group, and a cyclododecane-1,5-diyl group; a cyclotetradecanediyl group such as a cyclotetradecane-1,2-diyl group, a cyclotetradecane-1,3-diyl group, a cyclotetradecane-1,4-diyl group, a cyclotetradecane-1,5-diyl group, and a cyclotetradecane-1,7-diyl group; a cycloeicosanediyl group such as a cycloeicosane-1,2-diyl group and a cycloeicosane-1,10-diyl group; and the like.

Examples of the divalent fused alicyclic group having 10 to 30 carbon atoms include a decalindiyl group such as a decalin-2,5-diyl group and a decalin-2,7-diyl group; an adamantanediyl group such as an adamantane-1,2-diyl group and an adamantane-1,3-diyl group; a bicyclo[2.2.1]heptanediyl group such as a bicyclo[2.2.1]heptane-2,3-diyl group, a bicyclo[2.2.1]heptane-2,5-diyl group, and a bicyclo[2.2.1]heptane-2,6-diyl group; and the like.

These divalent alicyclic hydrocarbon groups may be substituted with a substituent at an arbitrary position. Examples of the substituent include those mentioned above in connection with the ring included in $A^{x1}$ and the like.

$A^2$ and $A^3$ are preferably a divalent alicyclic hydrocarbon group having 3 to 12 carbon atoms, more preferably a cycloalkanediyl group having 3 to 12 carbon atoms, still more preferably a group among the groups respectively represented by the following formulas (A31) to (A34), and particularly preferably the group represented by the formula (A32).

(A31)

(A32)

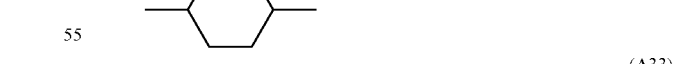
(A33)

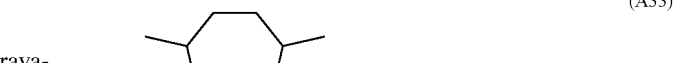

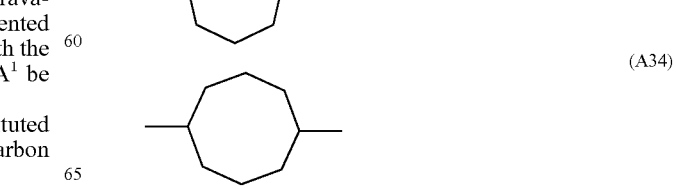
(A34)

The divalent alicyclic hydrocarbon group having 3 to 30 carbon atoms is classified into a cis-stereoisomer and a trans-stereoisomer based on the difference in the steric configuration of the carbon atom bonded to $Y^1$ and $Y^3$ (or $Y^2$ and $Y^4$). For example, a cyclohexane-1,4-diyl group is classified into a cis-isomer (A32a) and a trans-isomer (A32b) (see below).

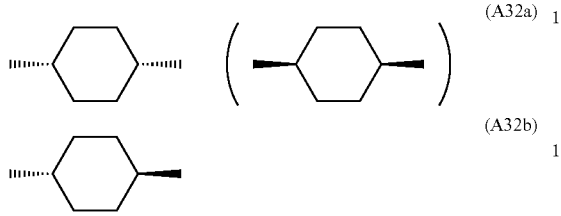

The divalent alicyclic hydrocarbon group having 3 to 30 carbon atoms may be a cis-isomer, a trans-isomer, or a mixture of a cis-isomer and a trans-isomer. Note that it is preferable that the divalent alicyclic hydrocarbon group having 3 to 30 carbon atoms be a trans-isomer or a cis-isomer, and more preferably a trans-isomer, since an excellent alignment capability can be obtained.

$A^4$ and $A^5$ are independently a substituted or unsubstituted divalent aromatic group having 4 to 30 carbon atoms.

The aromatic group represented by $A^4$ and $A^5$ may be a monocyclic aromatic group, or may be a polycyclic aromatic group.

Specific examples of $A^4$ and $A^5$ include, but are not limited to, the groups respectively represented by the following formulas.

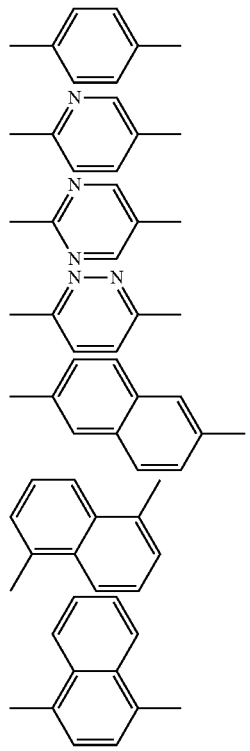

These aromatic groups (i.e., specific examples of $A^4$ and $A^5$) may be substituted with a substituent at an arbitrary position. Examples of the substituent include a halogen atom, a cyano group, a hydroxyl group, an alkyl group having 1 to 6 carbon atoms, an alkoxy group having 1 to 6 carbon atoms, a nitro group, a —C(=O)—OR group, and the like. Note that R is an alkyl group having 1 to 6 carbon atoms. Among these, a halogen atom, an alkyl group having 1 to 6 carbon atoms, and an alkoxy group having 1 to 6 carbon atoms are preferable as the substituent. A fluorine atom is preferable as the halogen atom. A methyl group, an ethyl group, and a propyl group are preferable as the alkyl group having 1 to 6 carbon atoms. A methoxy group and an ethoxy group are preferable as the alkoxy group having 1 to 6 carbon atoms.

It is preferable that $A^4$ and $A^5$ be independently a substituted or unsubstituted phenylene group, or a substituted or unsubstituted naphthylene group, more preferably a group among the groups respectively represented by the following formula (A41), (A42), and (A43) that are optionally substituted with a substituent, and particularly preferably the group represented by the formula (A41) that is optionally substituted with a substituent, in order to ensure that the intended effects of the invention can be more advantageously achieved.

 (A41)

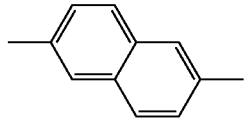 (A42)

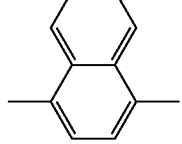 (A43)

$Q^1$ and $Q^2$ are independently a hydrogen atom, or a substituted or unsubstituted alkyl group having 1 to 6 carbon atoms.

Examples of the substituted or unsubstituted alkyl group having 1 to 6 carbon atoms include those mentioned above in connection with $A^{x1}$ and the like.

$Q^1$ and $Q^2$ are preferably a hydrogen atom or an alkyl group having 1 to 6 carbon atoms, and more preferably a hydrogen atom or a methyl group.

m and n are independently 0 or 1. It is preferable that both m and n be 0.

Note that the polymerizable compound according to one embodiment of the invention may be a stereoisomer based on the carbon-nitrogen double bond. These stereoisomers are also intended to be included within the scope of the invention.

The polymerizable compound according to one embodiment of the invention may be produced as described below, for example.

(1) Production Method 1

The polymerizable compound according to one embodiment of the invention in which $A^{x1}$ and $A^{x2}$ are identical with each other, and $A^{y1}$ and $A^{y2}$ are identical with each other, may be produced by effecting the following reaction, for example.

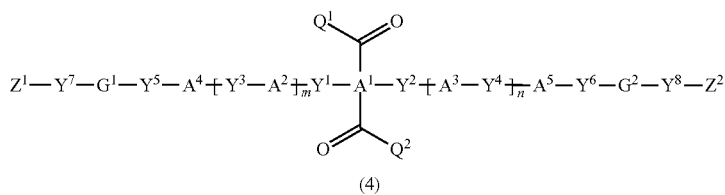

(4)

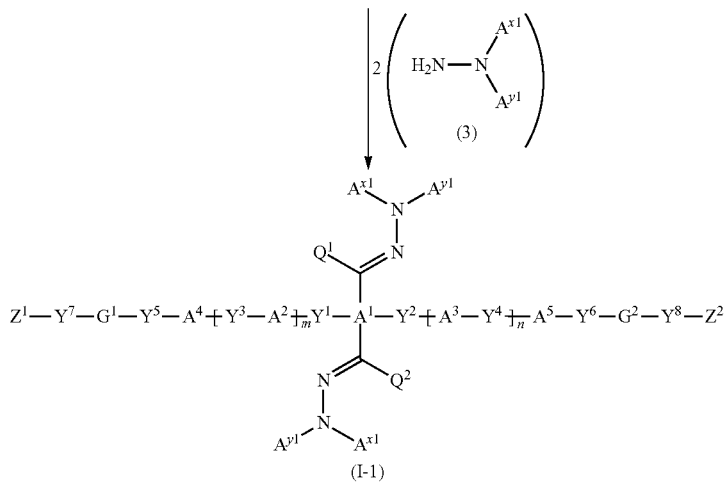

(I-1)

wherein $Y^1$ to $Y^8$, $G^1$, $G^2$, $Z^1$, $Z^2$, $A^{x1}$, $A^{y1}$, $A^1$ to $A^5$, $Q^1$, $Q^2$, m, and n are the same as defined above.

Specifically, the polymerizable compound represented by the formula (I-1) can be produced with high selectivity in high yield by reacting the carbonyl compound represented by the formula (4) (carbonyl compound (4)) with the hydrazine compound represented by the formula (3) (hydrazine compound (3)) in a molar ratio (carbonyl compound (4):hydrazine compound (3)) of 1:2 to 1:3.

The above reaction may be effected in the presence of an acid catalyst such as an organic acid (e.g., (±)-10-camphorsulfonic acid or p-toluenesulfonic acid), or an inorganic acid (e.g., hydrochloric acid or sulfuric acid). The addition of the acid catalyst may reduce the reaction time, and improve the yield. The acid catalyst is normally added in an amount of 0.001 to 1 mol based on 1 mol of the carbonyl compound (4). The acid catalyst may be added directly, or a solution prepared by dissolving the acid catalyst in an appropriate solvent may be added.

A solvent used for the above reaction is not particularly limited as long as the solvent is inert to the reaction. Examples of the solvent include an alcohol-based solvent such as methyl alcohol, ethyl alcohol, n-propyl alcohol, isopropyl alcohol, n-butyl alcohol, isobutyl alcohol, sec-butyl alcohol, and t-butyl alcohol; an ether-based solvent such as diethyl ether, tetrahydrofuran, 1,2-dimethoxyethane, 1,4-dioxane, and cyclopentyl methyl ether; an ester-based solvent such as ethyl acetate, propyl acetate, and methyl propionate; an aromatic hydrocarbon-based solvent such as benzene, toluene, and xylene; an aliphatic hydrocarbon-based solvent such as n-pentane, n-hexane, and n-heptane; an amide-based solvent such as N,N-dimethylformamide, N-methylpyrrolidone, and hexamethylphosphoric triamide; a sulfur-containing solvent such as dimethyl sulfoxide and sulfolane; a mixed solvent of two or more solvents among these solvents; and the like.

Among these, an alcohol-based solvent, an ether-based solvent, and a mixed solvent of an alcohol-based solvent and an ether-based solvent are preferable.

The solvent may be used in an appropriate amount taking account of the type of each compound, the reaction scale, and the like. The solvent is normally used in an amount of 1 to 100 g per gram of the hydrazine compound (3).

The reaction proceeds smoothly when the reaction temperature is within the range from −10° C. to the boiling point of the solvent. The reaction time is determined taking account of the reaction scale, and is normally several minutes to several hours.

The hydrazine compound (3) may be produced as described below.

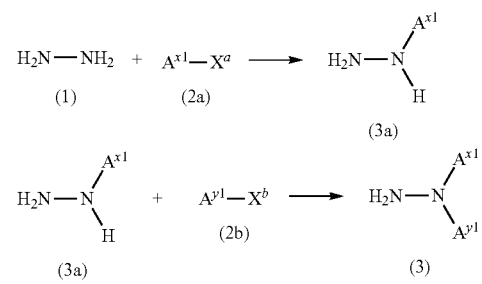

wherein $A^{x1}$ and $A^{y1}$ are the same as defined above, and $X^a$ and $X^b$ are independently a leaving group (e.g., halogen atom, methanesulfonyloxy group, or p-toluenesulfonyloxy group).

Specifically, the compound represented by the formula (2a) is reacted with the hydrazine (1) in an appropriate solvent in a molar ratio (compound (2a):hydrazine (1)) of 1:1 to 1:20 (preferably 1:2 to 1:10) to obtain the corresponding hydrazine compound (3a), and the hydrazine compound (3a) is reacted with the compound represented by the formula (2b) to obtain the hydrazine compound (3).

Hydrazine monohydrate is normally used as the hydrazine (1). A commercially available product may be used directly as the hydrazine (1).

A solvent used for the above reaction is not particularly limited as long as the solvent is inert to the reaction. Examples of the solvent include an alcohol-based solvent such as methyl alcohol, ethyl alcohol, n-propyl alcohol, isopropyl alcohol, n-butyl alcohol, isobutyl alcohol, sec-butyl alcohol, and t-butyl alcohol; an ether-based solvent such as diethyl ether, tetrahydrofuran, 1,2-dimethoxyethane, 1,4-dioxane, and cyclopentyl methyl ether; an aromatic hydrocarbon-based solvent such as benzene, toluene, and xylene; an aliphatic hydrocarbon-based solvent such as n-pentane, n-hexane, and n-heptane; an amide-based solvent such as N,N-dimethylformamide, N-methylpyrrolidone, and hexamethylphosphoric triamide; a sulfur-containing solvent such as dimethyl sulfoxide and sulfolane; a mixed solvent of two or more solvents among these solvents; and the like.

Among these, an alcohol-based solvent, an ether-based solvent, and a mixed solvent of an alcohol-based solvent and an ether-based solvent are preferable.

The solvent may be used in an appropriate amount taking account of the type of each compound, the reaction scale, and the like. The solvent is normally used in an amount of 1 to 100 g per gram of hydrazine.

The reaction proceeds smoothly when the reaction temperature is within the range from $-10°$ C. to the boiling point of the solvent. The reaction time is determined taking account of the reaction scale, and is normally several minutes to several hours.

The hydrazine compound (3) may also be produced by reducing the diazonium salt (5) (see below) using a known method.

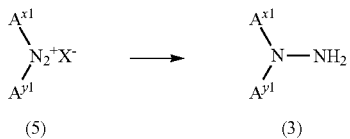

wherein $A^{x1}$ and $A^{y1}$ are the same as defined above, and $X^-$ is an anion that is a counter ion for diazonium. Examples of the anion represented by $X^-$ include an inorganic anion such as a hexafluorophosphoric acid ion, a fluoroboric acid ion, a chloride ion, and a sulfuric acid ion; an organic anion such as a polyfluoroalkylcarboxylic acid ion, a polyfluoroalkylsulfonic acid ion, a tetraphenylboric acid ion, an aromatic carboxylic acid ion, and an aromatic sulfonic acid ion; and the like.

Examples of a reducing agent used for the above reaction include a metal salt reducing agent.

The term "metal salt reducing agent" normally refers to a compound that includes a metal having a small valence, or a compound that includes a metal ion and a hydrido source (see "Yuki Gosei Jikkenhou Handbook (Handbook of Organic Synthesis Experiments)", 1990, edited by The Society of Synthetic Organic Chemistry, Japan, published by Maruzen Co., Ltd., p. 810).

Examples of the metal salt reducing agent include $NaAlH_4$, $NaAlH_p(Or)_q$ (wherein p and q are independently an integer from 1 to 3, provided that p+q=4, and r is an alkyl group having 1 to 6 carbon atoms), $LiAlH_4$, $iBu_2AlH$, $LiBH_4$, $NaBH_4$, $SnCl_2$, $CrCl_2$, $TiCl_3$, and the like.

The reduction reaction may be effected under known reaction conditions. For example, the reduction reaction may be effected under the reaction conditions described in JP-A-2005-336103, "Shin-Jikken Kagaku Koza (New Experimental Chemistry Course)", 1978, Vol. 14, published by Maruzen Co., Ltd., "Jikken Kagaku Koza (Experimental Chemistry Course)", 1992, Vol. 20, published by Maruzen Co., Ltd., or the like.

The diazonium salt (5) may be produced from aniline or the like using a known method.

The polymerizable compound according to one embodiment of the invention in which $A^{x1}$ and $A^{x2}$ differ from each other, and $A^{y1}$ and $A^{y2}$ differ from each other, may be produced by effecting the reaction stepwise. Specifically, the compound (3) (1 equivalent) is reacted with the compound (4), and a compound represented by the following formula (3') (1 equivalent) is reacted with the reaction product to obtain the target product.

wherein $A^{x2}$ and $A^{y2}$ are the same as defined above.

The polymerizable compound according to one embodiment of the invention in which $A^{x1}$ and $A^{y1}$ or $A^{x2}$ and $A^{y2}$ are bonded to each other to form a ring, may be produced by utilizing a compound represented by the following formula (3") as the compound (3), for example.

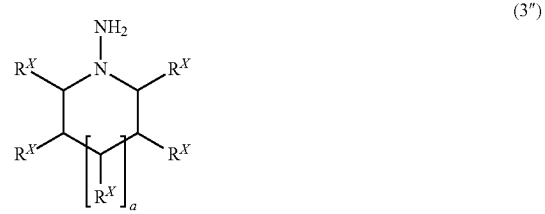

wherein $R^x$ and a are the same as defined above.

Many of the compounds represented by the formula (3") are known compounds, and may be produced using a known method (see JP-A-2005-289988, for example). A product commercially available as the compound represented by the formula (3") may be used after optional purification.

The carbonyl compound (4) may be produced by appropriately bonding and modifying a plurality of known compounds having the desired structure by arbitrarily combining an ether linkage (—O—)-forming reaction, an ester linkage (—C(=O)—O— or —O—C(=O)—)-forming reaction, a carbonate linkage (—O—C(=O)—O—)-forming reaction, and an amide linkage (—C(=O)NH— or —NHC(=O)—)-forming reaction.

An ether linkage may be formed as described below.
(i) A compound represented by D1-hal (wherein hal is a halogen atom; hereinafter the same) and a compound represented by D2-OMet (wherein Met is an alkali metal (mainly sodium); hereinafter the same) are mixed and condensed (Williamson synthesis). Note that D1 and D2 are an arbitrary organic group (hereinafter the same).
(ii) A compound represented by D1-hal and a compound represented by D2-OH are mixed and condensed in the presence of a base (e.g., sodium hydroxide or potassium hydroxide).

(iii) A compound represented by D1-J (wherein J is an epoxy group) and a compound represented by D2-OH are mixed and condensed in the presence of a base (e.g., sodium hydroxide or potassium hydroxide).
(iv) A compound represented by D1-OFN (wherein OFN is a group that includes an unsaturated bond) and a compound represented by D2-OMet are mixed and subjected to an addition reaction in the presence of a base (e.g., sodium hydroxide or potassium hydroxide).
(v) A compound represented by D1-hal and a compound represented by D2-OMet are mixed and condensed in the presence of copper or cuprous chloride (Ullmann condensation).

An ester linkage and an amide linkage may be formed as described below.
(vi) A compound represented by D1-COOH and a compound represented by D2-OH or D2-$NH_2$ are subjected to dehydration and condensation in the presence of a dehydration-condensation agent (e.g., N,N-dicyclohexylcarbodiimide).
(vii) A compound represented by D1-COOH is reacted with a halogenating agent to obtain a compound represented by D1-CO-hal, and the compound represented by D1-CO-hal is reacted with a compound represented by D2-OH or D2-$NH_2$ in the presence of a base.
(viii) A compound represented by D1-COOH is reacted with an acid anhydride to obtain a mixed acid anhydride, and the mixed acid anhydride is reacted with a compound represented by D2-OH or D2-$NH_2$.
(ix) A compound represented by D1-COOH and a compound represented by D2-OH or D2-$NH_2$ are subjected to dehydration and condensation in the presence of an acid catalyst or a base catalyst.

More specifically, the carbonyl compound (4) in which the group represented by $Z^2$—$Y^6$-$G^2$-$Y^4$-$A^3$-$Y^2$— is identical with the group represented by $Z^1$—$Y^5$-$G^1$-$Y^3$-$A^2$-$Y^1$—, and $Y^1$ is a group represented by $Y^{11}$—C(=O)—O— (hereinafter referred to as "compound (4')"), may be produced by effecting the following reaction.

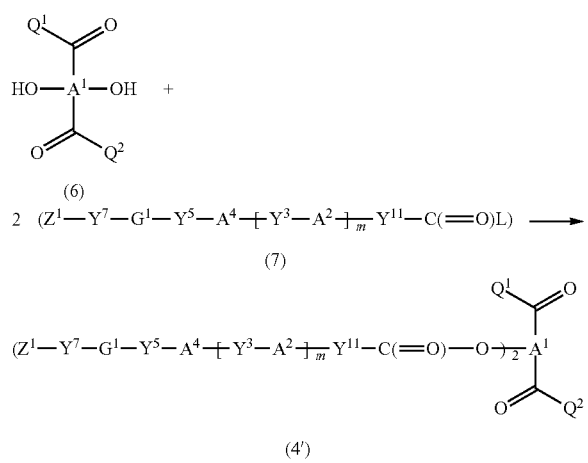

wherein $Y^3$, $Y^5$, $Y^7$, $G^1$, $Z^1$, $A^1$, $A^2$, $A^4$, $Q^1$, $Q^2$, and m are the same as defined above, $Y^{11}$ is a group provided that $Y^{11}$—C(=O)—O— is $Y^1$, $Y^1$ is the same as defined above, and L is a leaving group (e.g., hydroxyl group, halogen atom, methanesulfonyloxy group, or p-toluenesulfonyloxy group).

Specifically, the dihydroxy compound represented by the formula (6) (compound (6)) is reacted with the compound represented by the formula (7) (compound (7)) in a molar ratio (compound (6):compound (7)) of 1:2 to 1:4 (preferably 1:2 to 1:3) to produce the target compound (4') with high selectivity in high yield.

When the compound (7) is a compound (carboxylic acid) represented by the formula (7) in which L is a hydroxyl group, the target product may be obtained by effecting the reaction in the presence of a dehydration-condensation agent (e.g., 1-ethyl-3-(3-dimethylaminopropyl)carbodiimide hydrochloride or dicyclohexylcarbodiimide).

The dehydration-condensation agent is normally used in an amount of 1 to 3 mol based on 1 mol of the compound (7).

When the compound (7) is a compound (acid halide) represented by the formula (7) in which L is a halogen atom, the target product may be obtained by effecting the reaction in the presence of a base.

Examples of the base include an organic base such as triethylamine and pyridine; and an inorganic base such as sodium hydroxide, sodium carbonate, and sodium hydrogen carbonate.

The base is normally used in an amount of 1 to 3 mol based on 1 mol of the compound (7).

When the compound (7) is a compound (mixed acid anhydride) represented by the formula (7) in which L is a methanesulfonyloxy group or a p-toluenesulfonyloxy group, the target product may be obtained in the same manner as in the case where L is a halogen atom.

Examples of the solvent used for the above reaction include a chlorine-based solvent such as chloroform and methylene chloride; an amide-based solvent such as N-methylpyrrolidone, N,N-dimethylformamide, N,N-dimethylacetamide, and hexamethylphosphoric triamide; an ether-based solvent such as 1,4-dioxane, cyclopentyl methyl ether, tetrahydrofuran, tetrahydropyran, and 1,3-dioxolane; a sulfur-containing solvent such as dimethyl sulfoxide and sulfolane; an aromatic hydrocarbon-based solvent such as benzene, toluene, and xylene; an aliphatic hydrocarbon-based solvent such as n-pentane, n-hexane, and n-octane; an alicyclic hydrocarbon-based solvent such as cyclopentane and cyclohexane; a mixed solvent of two or more solvents among these solvents; and the like.

The solvent may be used in an appropriate amount taking account of the type of each compound, the reaction scale, and the like. The solvent is normally used in an amount of 1 to 50 g per gram of the hydroxy compound (6).

Many of the compounds (7) are known compounds. The carbonyl compound (7) may be produced by appropriately bonding and modifying a plurality of known compounds having a desired structure by arbitrarily combining an ether linkage (—O—)-forming reaction, an ester linkage (—C(=O)—O— or —O—C(=O)—)-forming reaction, a carbonate linkage (—O—C(=O)—O—)-forming reaction, and an amide linkage (—C(=O)NH— or —NHC(=O)—)-forming reaction.

Many of the compounds (6) are known compounds, and may be produced using a known method. For example, the compound (demethylated product) represented by the formula (6) in which $A^1$ is a trivalent benzene ring group, and $Q^1$ and $Q^2$ are a hydrogen atom, may be produced by sequentially adding an alkyllithium (e.g., n-butyllithium) and N,N-dimethylformamide to 1,4-dimethoxybenzene in the presence of a base (e.g., N,N,N',N'-tetramethylethylenediamine), stirring the mixture to obtain a formyl product, and reacting boron tribromide with the product. A product commercially available as the compound (6) may be used after optional purification.

(2) Production Method 2

The polymerizable compound according to one embodiment of the invention in which $A^{x1}$ and $A^{x2}$ are identical with each other, $A^{y1}$ and $A^{y2}$ are identical with each other, and —$Y^2$-$A^3$-$Y^4$-$G^2$-$Y^6$—$Z^2$ and —$Y^1$-$A^2$-$Y^3$-$G^1$-$Y^5$—$Z^1$ are identical with each other (i.e., a compound represented by the following formula (I-2)), may be produced by effecting the following reaction, for example.

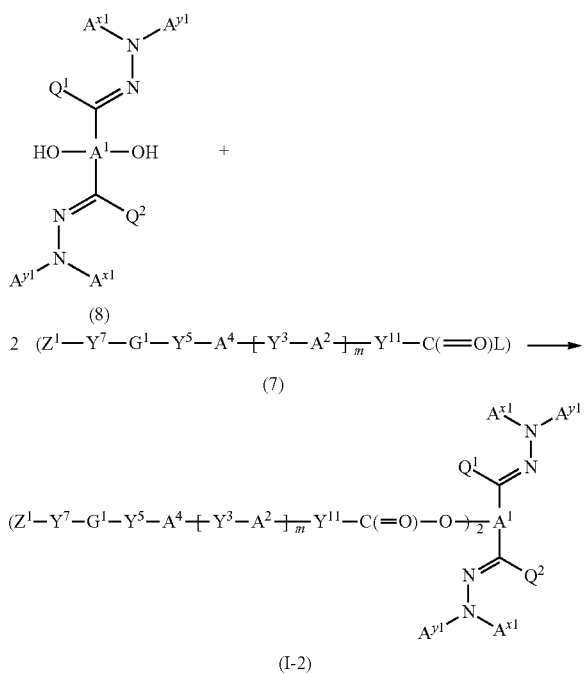

wherein $Y^3$, $Y^5$, $Y^7$, $G^1$, $Z^1$, $A^{x1}$, $A^{y1}$, $A^1$, $A^2$, $A^4$, $Q^1$, $Q^2$, L, $Y^{11}$, and m are the same as defined above.

Specifically, the hydrazide compound represented by the formula (8) (compound (8)) is reacted with the compound (7) in a molar ratio (compound (8):compound (7)) of 1:2 to 1:4 (preferably 1:2 to 1:3) to produce the target compound (I-2) with high selectivity in high yield.

The above reaction is effected under the same conditions as those employed when reacting the compound (6) and the compound (7).

The compound (8) may be produced as described below.

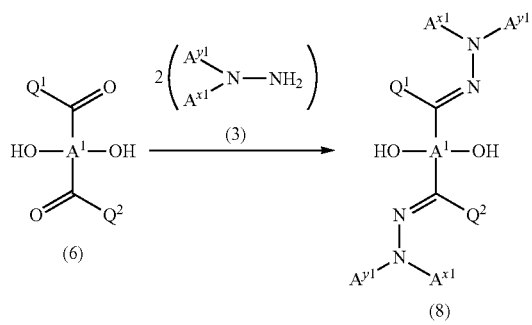

wherein $A^{x1}$, $A^{x2}$, $A^1$, $Q^1$, and $Q^2$ are the same as defined above.

Specifically, the compound (6) is reacted with the hydrazine compound (3) in a molar ratio (compound (6):compound (3)) of 1:2 to 1:4 (preferably 1:2 to 1:3) to produce the target compound (8) with high selectivity in high yield.

The above reaction is effected under the same conditions as those employed when reacting the carbonyl compound (4) and the hydrazine compound (3).

When producing the polymerizable compound according to one embodiment of the invention in which $A^{x1}$ and $A^{x2}$ differ from each other, and $A^{y1}$ and $A^{y2}$ differ from each other, a compound represented by the following formula (8') may be reacted with the compound (7) instead of the compound (8).

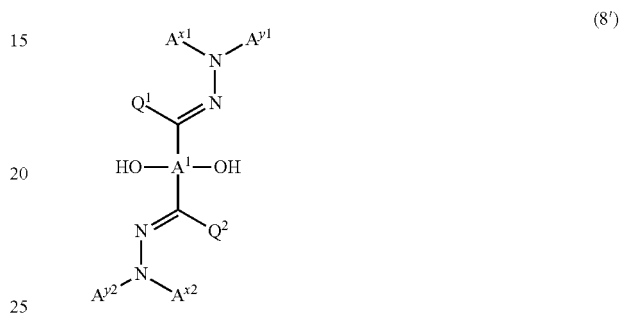

wherein $A^{x1}$, $A^{x2}$, $A^{y1}$, $A^{y2}$, $A^1$, $Q^1$, and $Q^2$ are the same as defined above.

The compound (8') may be produced by reacting the compound (3) (1 equivalent) with the compound (6), and reacting the compound represented by the formula (3') (1 equivalent) with the reaction product under the same reaction conditions.

After completion of the reaction, a post-treatment operation normally employed in synthetic organic chemistry is performed, optionally followed by a known separation/purification means such as column chromatography, recrystallization, or distillation to isolate the target product.

The structure of the target product may be identified by measurement (e.g., NMR spectrometry, IR spectrometry, or mass spectrometry), elemental analysis, and the like.

2) Polymerizable Composition

A polymerizable composition according to one embodiment of the invention includes at least one type of the polymerizable compound according to one embodiment of the invention. It is preferable that the polymerizable composition according to one embodiment of the invention further include an initiator. The initiator is used in order to more efficiently polymerize the polymerizable composition according to one embodiment of the invention.

The initiator may be appropriately selected taking account of the type of the polymerizable group included in the polymerizable compound. For example, a radical initiator may be used when the polymerizable group is a radically polymerizable group. An anionic initiator may be used when the polymerizable group is an anionically polymerizable group. A cationic initiator may be used when the polymerizable group is a cationically polymerizable group.

Examples of the radical initiator include a thermal radical generator that is a compound that generates active species that initiate polymerization of the polymerizable compound upon heating, and a photo-radical generator that is a compound that generates active species that initiate polymerization of the polymerizable compound upon exposure to exposure light (e.g., visible rays, ultraviolet rays (e.g., i-line), deep ultraviolet rays, electron beams, or X-rays). It is preferable to use the photo-radical generator.

Examples of the photo-radical generator include an acetophenone-based compound, a biimidazole-based compound, a triazine-based compound, an O-acyloxime-based compound, an onium salt-based compound, a benzoin-based compound, a benzophenone-based compound, an α-diketone-based compound, a polynuclear quinone-based compound, a xanthone-based compound, a diazo-based compound, an imide sulfonate-based compound, and the like. These compounds generate active radicals, or an active acid, or both active radicals and an active acid, upon exposure. These photo-radical generators may be used either alone or in combination.

Specific examples of the acetophenone-based compound include 2-hydroxy-2-methyl-1-phenylpropan-1-one, 2-methyl-1-[4-(methylthio)phenyl]-2-morpholinopropan-1-one, 2-benzyl-2-dimethylamino-1-(4-morpholinophenyl)butan-1-one, 1-hydroxycyclohexyl phenyl ketone, 2,2-dimethoxy-1,2-diphenylethan-1-one, 1,2-octanedione, 2-benzyl-2-dimethylamino-4'-morpholinobutyrophenone, and the like.

Specific examples of the biimidazole-based compound include 2,2'-bis(2-chlorophenyl)-4,4',5,5'-tetrakis(4-ethoxycarbonylphenyl)-1,2'-biimidazole, 2,2'-bis(2-bromophenyl)-4,4',5,5'-tetrakis(4-ethoxycarbonylphenyl)-1,2'-biimidazole, 2,2'-bis(2-chlorophenyl)-4,4',5,5'-tetraphenyl-1,2'-biimidazole, 2,2'-bis(2,4-dichlorophenyl)-4,4',5,5'-tetraphenyl-1,2'-biimidazole, 2,2'-bis(2,4,6-trichlorophenyl)-4,4',5,5'-tetraphenyl-1,2'-biimidazole, 2,2'-bis(2-bromophenyl)-4,4',5,5'-tetraphenyl-1,2'-biimidazole, 2,2'-bis(2,4-dibromophenyl)-4,4',5,5'-tetraphenyl-1,2'-biimidazole, 2,2'-bis(2,4,6-tribromophenyl)-4,4',5,5'-tetraphenyl-1,2'-biimidazole, and the like.

When using a biimidazole-based compound as a photoinitiator, it is preferable to use a hydrogen donor in combination with the biimidazole-based compound since sensitivity can be further improved.

The term "hydrogen donor" used herein refers to a compound that can donate a hydrogen atom to radicals generated by the biimidazole-based compound upon exposure. A mercaptan-based compound, an amine-based compound, and the like are preferable as the hydrogen donor.

Examples of the mercaptan-based compound include 2-mercaptobenzothiazole, 2-mercaptobenzoxazole, 2-mercaptobenzimidazole, 2,5-dimercapto-1,3,4-thiadiazole, 2-mercapto-2,5-dimethylaminopyridine, and the like. Examples of the amine-based compound include 4,4'-bis(dimethylamino)benzophenone, 4,4'-bis(diethylamino)benzophenone, 4-diethylaminoacetophenone, 4-dimethylaminopropiophenone, ethyl-4-dimethylaminobenzoate, 4-dimethylaminobenzoic acid, 4-dimethylaminobenzonitrile, and the like.

Specific examples of the triazine-based compound include a triazine-based compound that includes a halomethyl group, such as 2,4,6-tris(trichloromethyl)-s-triazine, 2-methyl-4,6-bis(trichloromethyl)-s-triazine, 2-[2-(5-methylfuran-2-yl)ethenyl]-4,6-bis(trichloromethyl)-s-triazine, 2-[2-(furan-2-yl)ethenyl]-4,6-bis(trichloromethyl)-s-triazine, 2-[2-(4-diethylamino-2-methylphenyl)ethenyl]-4,6-bis(trichloromethyl)-s-triazine, 2-[2-(3,4-dimethoxyphenyl)ethenyl]-4,6-bis(trichloromethyl)-s-triazine, 2-(4-methoxyphenyl)-4,6-bis(trichloromethyl)-s-triazine, 2-(4-ethoxystyryl)-4,6-bis(trichloromethyl)-s-triazine, and 2-(4-n-butoxyphenyl)-4,6-bis(trichloromethyl)-s-triazine.

Specific examples of the O-acyloxime-based compound include 1-[4-(phenylthio)phenyl]-heptane-1,2-dione-2-(O-benzoyloxime), 1-[4-(phenylthio)phenyl]-octane-1,2-dione-2-(O-benzoyloxime), 1-[4-(benzoyl)phenyl]-octane-1,2-dione-2-(O-benzoyloxime), 1-[9-ethyl-6-(2-methylbenzoyl)-9H-carbazol-3-yl]-ethanone-1-(O-acetyloxime), 1-[9-ethyl-6-(3-methylbenzoyl)-9H-carbazol-3-yl]-ethanone-1-(O-acetyloxime), 1-(9-ethyl-6-benzoyl-9h-carbazol-3-yl)-ethanone-1-(O-acetyloxime), ethanone-1-[9-ethyl-6-(2-methyl-4-tetrahydrofuranylbenzoyl)-9H-carbazol-3-yl]-1-(O-acetyloxime), ethanone-1-[9-ethyl-6-(2-methyl-4-tetrahydropyranylbenzoyl)-9H-carbazol-3-yl]-1-(O-acetyloxime), ethanone-1-[9-ethyl-6-(2-methyl-5-tetrahydrofuranylbenzoyl)-9H-carbazol-3-yl]-1-(O-acetyloxime), ethanone-1-[9-ethyl-6-(2-methyl-5-tetrahydropyranylbenzoyl)-9H-carbazol-3-yl]-1-(O-acetyloxime), ethanone-1-[9-ethyl-6-{2-methyl-4-(2,2-dimethyl-1,3-dioxolanyl)benzoyl}-9H-carbazol-3-yl]-1-(O-acetyloxime), ethanone-1-[9-ethyl-6-(2-methyl-4-tetrahydrofuranylmethoxybenzoyl)-9H-carbazol-3-yl]-1-(O-acetyloxime), ethanone-1-[9-ethyl-6-(2-methyl-4-tetrahydropyranylmethoxybenzoyl)-9H-carbazol-3-yl]-1-(O-acetyloxime), ethanone-1-[9-ethyl-6-(2-methyl-5-tetrahydrofuranylmethoxybenzoyl)-9H-carbazol-3-yl]-1-(O-acetyloxime), ethanone-1-[9-ethyl-6-(2-methylbenzoyl)-9H-carbazol-3-yl]-1-(O-acetyloxime), ethanone-1-[9-ethyl-6-(2-methyl-5-tetrahydropyranylmethoxybenzoyl)-9H-carbazol-3-yl]-1-(O-acetyloxime), ethanone-1-[9-ethyl-6-{2-methyl-4-(2,2-dimethyl-1,3-dioxolanyl)methoxybenzoyl}-9H-carbazol-3-yl]-1-(O-acetyloxime), and the like.

A commercially available product may be used directly as the photo-radical generator. Specific examples of a commercially available product that may be used as the photo-radical generator include Irgacure 907, Irgacure 184, Irgacure 369, Irgacure 651, Irgacure 819, Irgacure 907, and Irgacure OXE02 (manufactured by BASF); Adekaoptomer N1919 (manufactured by Adeka Corporation); and the like.

Examples of the anionic initiator include an alkyllithium compound; a monolithium salt or a monosodium salt of biphenyl, naphthalene, pyrene, and the like; a polyfunctional initiator such as a dilithium salt and a trilithium salt; and the like.

Examples of the cationic initiator include a proton acid such as sulfuric acid, phosphoric acid, perchloric acid, and trifluoromethanesulfonic acid; a Lewis acid such as boron trifluoride, aluminum chloride, titanium tetrachloride, and tin tetrachloride; an aromatic onium salt or a combination of an aromatic onium salt and a reducing agent; and the like.

These initiators may be used either alone or in combination.

The initiator is normally added to the polymerizable composition according to one embodiment of the invention in an amount of 0.1 to 30 parts by weight, and preferably 0.5 to 10 parts by weight, based on 100 parts by weight of the polymerizable compound.

It is preferable to add a surfactant to the polymerizable composition according to one embodiment of the invention in order to adjust surface tension. The surfactant is not particularly limited, but is preferably a nonionic surfactant. Examples of the nonionic surfactant include an oligomer having a molecular weight of about several thousand, such as KH-40 (manufactured by AGC Seimi Chemical Co., Ltd.). The surfactant is normally added to the polymerizable composition according to one embodiment of the invention in an amount of 0.01 to 10 parts by weight, and preferably 0.1 to 2 parts by weight, based on 100 parts by weight of the polymerizable compound.

The polymerizable composition according to one embodiment of the invention may further include an additional additive such as an additional copolymerizable monomer, a metal, a metal complex, a dye, a pigment, a fluorescent material, a phosphorescent material, a leveling agent, a thixotropic agent, a gelling agent, a polysaccharide, a UV absorber, an IR (infrared) absorber, an antioxidant, an ion-exchange resin, or a metal oxide (e.g., titanium oxide). Each additive is normally added to the polymerizable composition according to one embodiment of the invention in an amount of 0.1 to 20 parts by weight based on 100 parts by weight of the polymerizable compound.

The polymerizable composition according to one embodiment of the invention may be prepared by mixing and dissolving given amounts of the polymerizable compound according to one embodiment of the invention, the initiator, and an optional additive in an appropriate organic solvent.

Examples of the organic solvent include a ketone such as cyclopentanone, cyclohexanone, and methyl ethyl ketone; an acetate such as butyl acetate and amyl acetate; a halogenated hydrocarbon such as chloroform, dichloromethane, and dichloroethane; an ether such as 1,4-dioxane, cyclopentyl methyl ether, tetrahydrofuran, tetrahydropyran, and 1,3-dioxolane; and the like.

The polymerizable composition thus obtained is useful as a raw material for producing a polymer according to one embodiment of the invention, or an optically anisotropic article according to one embodiment of the invention (described below).

3) Polymer

A polymer according to one embodiment of the invention is (1) a polymer obtained by polymerizing the polymerizable compound according to one embodiment of the invention, or (2) a polymer obtained by polymerizing the polymerizable composition according to one embodiment of the invention.

The term "polymerization" used herein refers to a chemical reaction in a broad sense including a normal polymerization reaction and a crosslinking reaction.

(1) Polymer Obtained by Polymerizing Polymerizable Compound

The polymer obtained by polymerizing the polymerizable compound according to one embodiment of the invention may be a homopolymer of the polymerizable compound according to one embodiment of the invention, a copolymer of two or more types of the polymerizable compound according to one embodiment of the invention, or a copolymer of the polymerizable compound according to one embodiment of the invention and an additional copolymerizable monomer.

Examples of the additional copolymerizable monomer include, but are not limited to, 4'-methoxyphenyl 4-(2-methacryloyloxyethyloxyl)benzoate, biphenyl 4-(6-methacryloyloxyhexyloxyl)benzoate, 4'-cyanobiphenyl 4-(2-acryloyloxyethyloxyl)benzoate, 4'-cyanobiphenyl 4-(2-methacryloyloxyethyloxyl)benzoate, 3',4'-difluorophenyl 4-(2-methacryloyloxyethyloxyl)benzoate, naphthyl 4-(2-methacryloyloxyethyloxyl)benzoate, 4-acryloyloxy-4'-decylbiphenyl, 4-acryloyloxy-4'-cyanobiphenyl, 4-(2-acryloyloxyethyloxy)-4'-cyanobiphenyl, 4-(2-methacryloyloxyethyloxy)-4'-methoxybiphenyl, 4-(2-methacryloyloxyethyloxy)-4'-(4''-fluorobenzyloxy)-biphenyl, 4-acryloyloxy-4'-propylcyclohexylphenyl, 4-methacryloyl-4'-butylbicyclohexyl, 4-acryloyl-4'-amylotolan, 4-acryloyl-4'-(3,4-difluorophenyl)bicyclohexyl, (4-amylphenyl) 4-(2-acryloyloxyethyl)benzoate, (4-(4'-propylcyclohexyl)phenyl) 4-(2-acryloyloxyethyl)benzoate, and the like.

Examples of a commercially available product that may be used as the additional copolymerizable monomer include LC-242 (manufactured by BASF) and the like. The compounds disclosed in JP-A-2007-002208, JP-A-2009-173893, JP-A-2009-274984, JP-A-2010-030979, JP-A-2010-031223, JP-A-2011-006360, and the like may also be used as the additional copolymerizable monomer.

A polyfunctional monomer that includes a plurality of polymerizable unsaturated groups (e.g., acryloyl group, methacryloyl group, vinyl group, and allyl group) may also be used as the additional copolymerizable monomer.

Examples of such a polyfunctional monomer include an alkanediol diacrylate such as 1,2-butanediol diacrylate, 1,3-butanediol diacrylate, 1,4-butanediol diacrylate, neopentanediol diacrylate, and 1,6-hexanediol diacrylate, an alkanediol dimethacrylate such as 1,2-butanediol dimethacrylate, 1,3-butanediol dimethacrylate, 1,4-butanediol dimethacrylate, neopentanediol dimethacrylate, and 1,6-hexanediol dimethacrylate, a polyethylene glycol diacrylate such as ethylene glycol diacrylate, diethylene glycol diacrylate, triethylene glycol diacrylate, and tetraethylene glycol diacrylate, a polypropylene glycol diacrylate such as propylene glycol diacrylate, dipropylene glycol diacrylate, tripropylene glycol diacrylate, and tetrapropylene glycol diacrylate, a polyethylene glycol dimethacrylate such as ethylene glycol dimethacrylate, diethylene glycol dimethacrylate, triethylene glycol dimethacrylate, and tetraethylene glycol dimethacrylate, a polypropylene glycol dimethacrylate such as propylene glycol dimethacrylate, dipropylene glycol dimethacrylate, tripropylene glycol dimethacrylate, and tetrapropylene glycol dimethacrylate, a polyethylene glycol divinyl ether such as ethylene glycol divinyl ether, diethylene glycol divinyl ether, triethylene glycol divinyl ether, and tetraethylene glycol divinyl ether, a polyethylene glycol diallyl ether such as ethylene glycol diallyl ether, diethylene glycol diallyl ether, triethylene glycol diallyl ether, and tetraethylene glycol diallyl ether, bisphenol F ethoxylate diacrylate, bisphenol F ethoxylate dimethacrylate, bisphenol A ethoxylate diacrylate, bisphenol A ethoxylate dimethacrylate, trimethylolpropane triacrylate, trimethylolpropane trimethacrylate, trimethylolpropane ethoxylate triacrylate, trimethylolpropane ethoxylate trimethacrylate, trimethylolpropane propoxylate triacrylate, trimethylolpropane propoxylate trimethacrylate, isocyanuric acid ethoxylate triacrylate, glycerol ethoxylate triacrylate, glycerol propoxylate triacrylate, pentaerythritol ethoxylate tetraacrylate, ditrimethylolpropane ethoxylate tetraacrylate, dipentaerythritol ethoxylate hexacrylate, and the like.

The polymerizable compound according to one embodiment of the invention may be (co)polymerized optionally together with the additional copolymerizable monomer in the presence of an appropriate initiator. The initiator may be used in an amount similar to that of the initiator included in the polymerizable composition.

When the polymer according to one embodiment of the invention is a copolymer of the polymerizable compound according to one embodiment of the invention and the additional copolymerizable monomer, the content of structural units derived from the polymerizable compound according to one embodiment of the invention is not particularly limited, but is preferably 50 wt % or more, and more preferably 70 wt % or more, based on the total structural units. When the content of structural units derived from the polymerizable compound is within the above range, a polymer that has a high glass transition temperature (Tg) and high hardness can be obtained.

The polymer (1) may be produced by (A) (co)polymerizing the polymerizable compound optionally together with the additional copolymerizable monomer in an appropriate organic solvent in the presence of an appropriate initiator, isolating the target polymer, dissolving the polymer in an appropriate organic solvent to prepare a solution, applying the solution to an appropriate substrate to obtain a film, and drying the film, followed by optional heating, or (B) applying a solution prepared by dissolving the polymerizable compound and an initiator in an organic solvent optionally together with the additional copolymerizable monomer to a substrate using a known coating method, removing the solvent, and effecting polymerization by applying heat or activated energy rays, for example.

Examples of the initiator include those mentioned above in connection with the initiator included in the polymerizable composition.

The organic solvent used for polymerization when using the method (A) is not particularly limited as long as the organic solvent is inert. Examples of the organic solvent include an aromatic hydrocarbon such as toluene, xylene, and mesitylene; a ketone such as cyclohexanone, cyclopentanone, and methyl ethyl ketone; an acetate such as butyl acetate and amyl acetate; a halogenated hydrocarbon such as chloroform, dichloromethane, and dichloroethane; an ether such as cyclopentyl methyl ether, tetrahydrofuran, and tetrahydropyran; and the like. Among these, it is preferable to use a compound having a boiling point of 60 to 250° C., and preferably 60 to 150° C., from the viewpoint of handling capability.

Examples of the organic solvent used to dissolve the polymer when implementing the method (A), and the organic solvent used for the method (B), include a ketone-based solvent such as acetone, methyl ethyl ketone, methyl isobutyl ketone, cyclopentanone, and cyclohexanone; an ester-based solvent such as butyl acetate and amyl acetate; a halogenated hydrocarbon-based solvent such as dichloromethane, chloroform, and dichloroethane; an ether-based solvent such as tetrahydrofuran, tetrahydropyran, 1,2-dimethoxyethane, 1,4-dioxane, cyclopentyl methyl ether, 1,3-dioxolane; an aprotic polar solvent such as N,N-dimethylformamide, N,N-dimethylacetamide, dimethyl sulfoxide, gamma-butyrolactone, and N-methylpyrrolidone; and the like. Among these, it is preferable to use a compound having a boiling point of 60 to 200° C. from the viewpoint of handling capability. These solvents may be used either alone or in combination.

A substrate formed of a known organic or inorganic material may be used as the substrate. Examples of the organic material include a polycycloolefin (e.g., Zeonex and Zeonor (registered trademark; manufactured by Zeon Corporation); Arton (registered trademark; manufactured by JSR Corporation); and Apel (registered trademark; manufactured by Mitsui Chemicals Inc.)), polyethylene terephthalate, a polycarbonate, a polyimide, a polyamide, polymethyl methacrylate, polystyrene, polyvinyl chloride, polytetrafluoroethylene, cellulose, cellulose triacetate, polyethersulfone, and the like. Examples of the inorganic material include silicon, glass, calcite, and the like. It is preferable to use an organic material.

The substrate may be a single-layer substrate, or may be a laminate.

The substrate is preferably a substrate that is formed of an organic material, and more preferably a resin film that is formed of the organic material.

The polymer solution (method (A)) or the solution subjected to polymerization (method (B)) may be applied to the substrate using a known coating method. Examples of the coating method include a curtain coating method, an extrusion coating method, a roll coating method, a spin coating method, a dip coating method, a bar coating method, a spray coating method, a slide coating method, a print coating method, and the like.

(2) Polymer Obtained by Polymerizing Polymerizable Composition

The polymer according to one embodiment of the invention can be easily obtained by polymerizing the polymerizable composition according to one embodiment of the invention. It is preferable to use the polymerizable composition that includes the initiator (particularly a photoinitiator) in order to more efficiently effect polymerization.

Specifically, it is preferable to produce the polymer according to one embodiment of the invention using the method (B) that applies the polymerizable composition according to one embodiment of the invention to a substrate, and polymerizes the applied polymerizable composition. Examples of the substrate include a substrate used to produce an optically anisotropic article (described later), and the like.

The polymerizable composition according to one embodiment of the invention may be applied to the substrate using a known coating method (e.g., bar coating method, spin coating method, roll coating method, gravure coating method, spray coating method, die coating method, cap coating method, or dipping method). A known organic solvent may be added to the polymerizable composition according to one embodiment of the invention in order to improve the applicability of the polymerizable composition. In this case, it is preferable to remove the organic solvent by natural drying, drying by heating, drying under reduced pressure, drying by heating under reduced pressure, or the like, after applying the polymerizable composition to the substrate.

The polymerizable compound according to one embodiment of the invention or the polymerizable composition according to one embodiment of the invention may be polymerized by applying activated energy rays, or utilizing a thermal polymerization method, for example. It is preferable to polymerize the polymerizable compound or the polymerizable composition by applying activated energy rays since heating is unnecessary (i.e., the reaction can be effected at room temperature). It is preferable to apply light (e.g., ultraviolet rays) to the polymerizable compound or the polymerizable composition since the operation is simple.

The temperature when applying light is preferably set to 30° C. or less. The irradiance is normally 1 $W/m^2$ to 10 $kW/m^2$, and preferably 5 $W/m^2$ to 2 $kW/m^2$.

A polymer obtained by polymerizing the polymerizable compound according to one embodiment of the invention or the polymerizable composition according to one embodiment of the invention may be removed from the substrate, and used alone, or may be used directly as an optical film organic material or the like without removing the polymer from the substrate.

The number average molecular weight of the polymer according to one embodiment of the invention thus obtained is preferably 500 to 500,000, and more preferably 5000 to 300,000. When the number average molecular weight of the polymer is within the above range, the resulting film exhibits high hardness and an excellent handling capability. The number average molecular weight of the polymer may be determined by gel permeation chromatography (GPC) using monodisperse polystyrene as a standard (eluant: tetrahydrofuran).

It is considered that the polymer according to one embodiment of the invention has a structure in which crosslinking points are uniformly present within the molecule, and exhibits a high crosslinking efficiency and excellent hardness.

The polymer according to one embodiment of the invention makes it possible to inexpensively produce an optical film that achieves uniform conversion of polarized light over a wide wavelength band, and exhibits satisfactory performance.

4) Optically Anisotropic Article

An optically anisotropic article according to one embodiment of the invention includes the polymer according to one embodiment of the invention.

The optically anisotropic article according to one embodiment of the invention may be obtained by forming an alignment film on a substrate, and forming a liquid crystal layer on the alignment film using the polymer according to one embodiment of the invention.

The alignment film is formed on the surface of the substrate in order to achieve in-plane alignment of an organic semiconductor compound in one direction.

The alignment film may be obtained by applying a solution (alignment film composition) that includes a polymer (e.g., polyimide, polyvinyl alcohol, polyester, polyallylate, polyamideimide, or polyetherimide) to the substrate to form a film, drying the film, and subjecting the film to a rubbing treatment in one direction, for example.

The thickness of the alignment film is preferably 0.001 to 5 μm, and more preferably 0.001 to 1 μm.

The rubbing treatment may be performed on the alignment film or the substrate. The rubbing treatment may be implemented using an arbitrary method. For example, the alignment film may be rubbed in a given direction using a roll around which a cloth or felt formed of synthetic fibers (e.g., nylon) or natural fibers (e.g., cotton) is wound. It is preferable to wash the alignment film with isopropyl alcohol or the like after the rubbing treatment in order to remove a fine powder (foreign substance) formed during the rubbing treatment, and clean the surface of the alignment film.

The alignment film may be provided with a function of achieving in-plane alignment of a cholesteric liquid crystal layer in one direction by applying polarized UV rays to the surface of the alignment film.

The liquid crystal layer may be formed on the alignment film using the polymer according to one embodiment of the invention by utilizing the method described above in connection with the polymer according to one embodiment of the invention.

Since the optically anisotropic article according to one embodiment of the invention is produced using the polymer according to one embodiment of the invention, the optically anisotropic article can be produced at low cost, achieves uniform conversion of polarized light over a wide wavelength band, and exhibits satisfactory performance.

Examples of the optically anisotropic article according to one embodiment of the invention include a retardation film, an alignment film for a liquid crystal display device (liquid crystal display), a polarizer, a viewing angle enhancement film, a color filter, a low-pass filter, an optical polarization prism, an optical filter, and the like.

EXAMPLES

The invention is further described below by way of examples. Note that the invention is not limited to the following examples.

Example 1: Synthesis of Compound 1

Compound 1

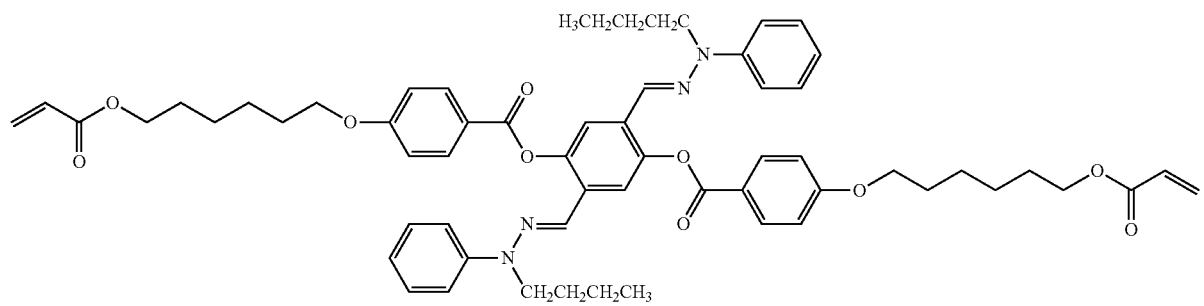

Step 1: Synthesis of Intermediate A

Intermediate A

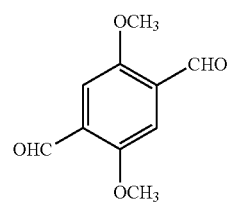

A three-necked reactor equipped with a thermometer was charged with 7.0 g (50.67 mmol) of 1,4-dimethoxybenzene, 29.44 g (253.33 mmol) of N,N,N',N'-tetramethylethylenediamine, and 280 ml of diethyl ether under a nitrogen stream to prepare a homogeneous solution. After cooling the solution to 0° C., 97.4 ml (253.33 mmol) of 2.6 M n-butyllithium (n-hexane solution) was added dropwise to the solution over 30 minutes. After the dropwise addition, the reaction mixture was reacted for 5 hours under reflux, and then cooled to −78° C. After the addition of 18.52 g (253.33 mmol) of N,N-dimethylformamide, the mixture was stirred at −78° C. for 1 hour. After the addition of 350 ml of a 3 N hydrochloric acid aqueous solution to the reaction mixture at −78° C., the mixture was heated to 25° C., and 300 ml of distilled water and 200 ml of a saturated sodium chloride solution were added to the mixture, followed by extraction with 700 ml of chloroform. The chloroform layer was dried over anhydrous sodium sulfate, and sodium sulfate was filtered off. The solvent was evaporated from the filtrate under reduced pressure using a rotary evaporator. The resulting solid was added to 100 ml of toluene. After stirring the mixture for 5 minutes, the resulting crystals were filtered off to obtain 6.1 g of an intermediate A as yellow crystals (yield: 62%).

The structure of the target product was identified by $^1$H-NMR.

$^1$H-NMR (500 MHz, CDCl$_3$, TMS, δ ppm): 10.51 (s, 2H), 7.46 (s, 2H), 3.95 (s, 6H).

Step 2: Synthesis of Intermediate B

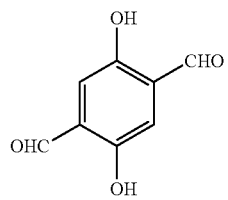

Intermediate B

A three-necked reactor equipped with a thermometer was charged with 3.32 g (17.10 mmol) of the intermediate A synthesized in the step 1 and 160 ml of dichloromethane under a nitrogen stream to prepare a solution, which was cooled to −40° C. After the addition of 51.3 ml (51.29 mmol) of boron tribromide (17% dichloromethane solution) dropwise to the solution, the mixture was stirred at −40° C. for 1 hour. The reaction mixture was then heated to 25° C., and stirred for 2 hours. 600 ml of ice water was added to the reaction mixture, followed by extraction twice with 500 ml of ethyl acetate. The organic layer was collected, and dried over anhydrous sodium sulfate, and sodium sulfate was filtered off. The solvent was evaporated from the filtrate under reduced pressure using a rotary evaporator. The resulting solid was added to 100 ml of toluene. After stirring the mixture for 5 minutes, the resulting crystals were filtered off to obtain 2.67 g of an intermediate B as yellow crystals (yield: 94%).

The structure of the target product was identified by $^1$H-NMR.

$^1$H-NMR (500 MHz, CDCl$_3$, TMS, δ ppm): 10.23 (s, 2H), 9.96 (s, 2H), 7.24 (s, 2H).

Step 3: Synthesis of Intermediate C

A three-necked reactor equipped with a thermometer was charged with 6.41 g (21.91 mmol) of 4-(6-acryloylhex-1-yloxy)benzoic acid (manufactured by DKSH Japan K.K.) and 50 ml of tetrahydrofuran (THF) under a nitrogen stream to prepare a homogeneous solution. After the addition of 2.56 g (22.33 mmol) of methanesulfonyl chloride to the solution, the reactor was immersed in a water bath to adjust the temperature of the reaction mixture to 20° C. 2.30 g (22.75 mmol) of triethylamine was added dropwise to the reaction mixture over 5 minutes while maintaining the temperature of the reaction mixture at 20 to 25° C. After removing the reactor from the water bath, the reaction mixture was stirred at 25° C. for 1.5 hours. After the addition of 0.21 g (1.69 mmol) of 4-(dimethylamino)pyridine and 1.40 g (8.43 mmol) of the intermediate B, the reactor was immersed in a water bath to adjust the temperature of the reaction mixture to 20° C. 2.13 g (21.07 mmol) of triethylamine was added dropwise to the reaction mixture over 5 minutes while maintaining the temperature of the reaction mixture at 20 to 25° C. After the dropwise addition, the mixture was stirred at 25° C. for 2 hours. After completion of the reaction, 300 ml of distilled water and 100 ml of a saturated sodium chloride solution were added to the reaction mixture, followed by extraction twice with 500 ml of chloroform. The organic layer was collected, and dried over anhydrous sodium sulfate, and sodium sulfate was filtered off. The solvent was evaporated from the filtrate under reduced pressure using a rotary evaporator. The residue was purified by silica gel column chromatography (chloroform:THF=9:1) to obtain 4.29 g of a compound C as a white solid (yield: 71%).

The structure of the target product was identified by $^1$H-NMR.

$^1$H-NMR (500 MHz, DMSO-d$_6$, TMS, δ ppm): 10.25 (s, 2H), 8.18 (d, 4H, J=9.0 Hz), 7.91 (s, 2H), 7.01 (d, 4H, J=9.0 Hz), 6.41 (dd, 2H, J=1.5 Hz, 17.5 Hz), 6.13 (dd, 2H, J=10.5 Hz, 17.5 Hz), 5.83 (dd, 2H, J=1.5 Hz, 10.5 Hz), 4.19 (t, 4H, J=6.5 Hz), 4.08 (t, 4H, J=6.5 Hz), 1.82-1.91 (m, 4H), 1.69-1.78 (m, 4H), 1.44-1.60 (m, 8H).

Step 4: Synthesis of Compound 1

A three-necked reactor equipped with a thermometer was charged with 1.40 g (1.96 mmol) of the intermediate C synthesized in the step 3 and 50 ml of THF under a nitrogen stream to prepare a solution. After the addition of 0.40 ml (0.40 mmol) of 1 N hydrochloric acid to the solution, 0.66 g (4.02 mmol) of 1-butyl-1-phenylhydrazine was added dropwise to the mixture over 10 minutes. The mixture was stirred at 25° C. for 1 hour. After the addition of 0.24 g (1.46 mmol) of 1-butyl-1-phenylhydrazine, the mixture was stirred for 2 hours. The reaction mixture was concentrated using a rotary evaporator, and the concentrate was purified by silica gel column chromatography (chloroform:THF=98:2 (volume ratio (hereinafter the same))) to obtain 1.84 g of a compound 1 as a yellow solid (yield: 93%).

Intermediate C

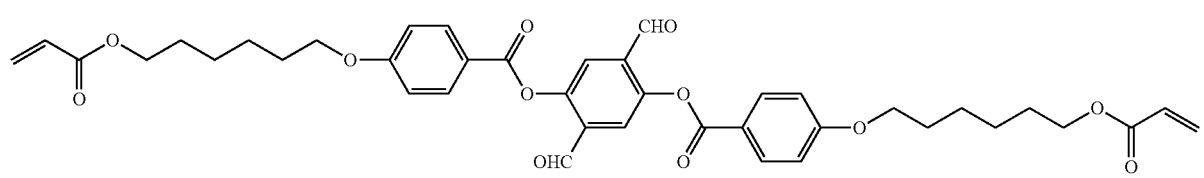

The structure of the target product was identified by $^1$H-NMR.

$^1$H-NMR (500 MHz, DMSO-d$_6$, TMS, δ ppm): 8.23 (d, 4H, J=9.0 Hz), 7.86 (s, 2H), 7.49 (s, 2H), 7.21-7.31 (m, 8H), 7.01 (d, 4H, J=9.0 Hz), 6.89 (t, 2H, J=7.0 Hz), 6.42 (dd, 2H, J=1.5 Hz, 17.5 Hz), 6.14 (dd, 2H, J=10.5 Hz, 17.5 Hz), 5.83 (dd, 2H, J=1.5 Hz, 10.5 Hz), 4.20 (t, 4H, J=6.5 Hz), 4.08 (t, 4H, J=6.5 Hz), 3.75 (t, 4H, J=8.0 Hz), 1.82-1.91 (m, 4H), 1.70-1.79 (m, 4H), 1.44-1.61 (m, 12H), 1.09-1.20 (m, 4H), 0.75 (t, 6H, J=7.5 Hz).

Example 2: Synthesis of Compound 2

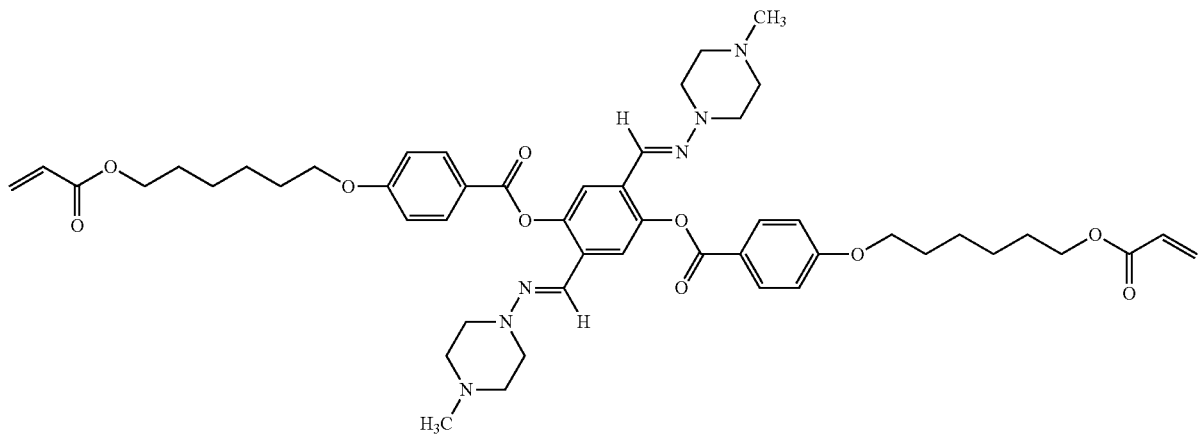

Compound 2

A three-necked reactor equipped with a thermometer was charged with 5.0 g (7.0 mmol) of the intermediate C synthesized in the step 3 of Example 1 and 50 ml of THF under a nitrogen stream to prepare a homogeneous solution. After the addition of 1.4 ml (1.4 mmol) of 1 N hydrochloric acid to the solution, 2.4 g (21.0 mmol) of 1-amino-4-methylpiperazine was added dropwise to the mixture at 25° C. over 15 minutes. After the dropwise addition, the mixture was stirred at 25° C. for 5 hours. After completion of the reaction, 300 ml of distilled water and 150 ml of a saturated sodium chloride solution were added to the reaction mixture, followed by extraction twice with 200 ml of ethyl acetate. The organic layer was collected, and dried over anhydrous sodium sulfate, and sodium sulfate was filtered off. The solvent was evaporated from the filtrate under reduced pressure using a rotary evaporator. The residue was purified by silica gel column chromatography (toluene:THF=1:1) to obtain 1.7 g of a compound 2 as a light yellow solid (yield: 27%).

The structure of the target product was identified by $^1$H-NMR.

$^1$H-NMR (500 MHz, CDCl$_3$, TMS, δ ppm): 8.16 (d, 4H, J=9.0 Hz), 7.68 (s, 2H), 7.47 (s, 2H), 6.98 (d, 4H, J=9.0 Hz), 6.41 (dd, 2H, J=1.5 Hz, 17.5 Hz), 6.13 (dd, 2H, J=10.5 Hz, 17.5 Hz), 5.83 (dd, 2H, J=1.5 Hz, 10.5 Hz), 4.19 (t, 4H, J=6.5 Hz), 4.06 (t, 4H, J=6.5 Hz), 3.09 (t, 8H, J=5.0 Hz), 2.50 (t, 8H, J=5.0 Hz), 2.29 (s, 6H), 1.81-1.89 (m, 4H), 1.69-1.78 (m, 4H), 1.44-1.59 (m, 8H).

Example 3: Synthesis of Compound 3

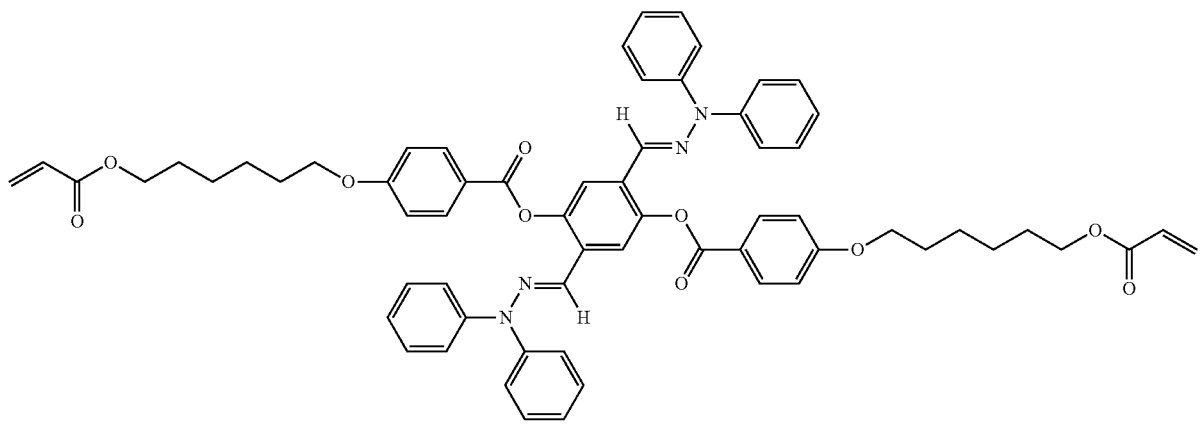

Compound 3

A three-necked reactor equipped with a thermometer was charged with 1.0 g (1.4 mmol) of the intermediate C synthesized in the step 3 of Example 1, 30 ml of THF, and 3 ml of methanol under a nitrogen stream to prepare a homogeneous solution. After the addition of 0.92 g (4.2 mmol) of 1,1-diphenylhydrazine hydrochloride to the solution over 10 minutes, the mixture was stirred at 25° C. for 1 hour, and then stirred at 40° C. for 2 hours. After completion of the reaction, 150 ml of distilled water and 150 ml of saturated sodium bicarbonate water were added to the reaction mixture, followed by extraction twice with 200 ml of ethyl acetate. The organic layer was collected, and dried over anhydrous sodium sulfate, and sodium sulfate was filtered off. The reaction mixture was concentrated using a rotary evaporator, and the concentrate was purified by silica gel column chromatography (chloroform:THF=98:2) to obtain 1.34 g of a compound 3 as a yellow solid (yield: 91%).

The structure of the target product was identified by $^1$H-NMR.

$^1$H-NMR (500 MHz, CDCl$_3$, TMS, δ ppm): 7.89 (d, 4H, J=9.0 Hz), 7.85 (s, 2H), 7.22-7.28 (m, 8H), 7.15 (s, 2H), 7.09 (d, 8H, J=7.5 Hz), 7.03 (t, 4H, J=7.5 Hz), 6.91 (d, 4H, J=9.0 Hz), 6.42 (dd, 2H, J=1.5 Hz, 17.5 Hz), 6.14 (dd, 2H, J=10.5 Hz, 17.5 Hz), 5.84 (dd, 2H, J=1.5 Hz, 10.5 Hz), 4.22 (t, 4H, J=6.5 Hz), 4.10 (t, 4H, J=6.5 Hz), 1.86-1.94 (m, 4H), 1.73-1.81 (m, 4H), 1.47-1.64 (m, 8H).

Reference Example 1: Synthesis of Compound A homogeneous solution. After the addition of 83.3 g (434.4 mmol) of 1-ethyl-3-(3-dimethylaminopropyl)carbodiimide hydrochloride (WSC) to the solution, the mixture was stirred at 25° C. for 12 hours. After completion of the reaction, the reaction mixture was added to 1.5 l of water, followed by extraction with 500 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=9:1) to obtain 75 g of an intermediate D as a white solid (yield: 75.4%).

The structure of the target product was identified by $^1$H-NMR.

$^1$H-NMR (400 MHz, CDCl$_3$, TMS, δ ppm): 10.20 (s, 1H), 8.18-8.12 (m, 4H), 7.78 (d, 1H, J=2.8 Hz), 7.52 (dd, 1H, J=2.8 Hz, 8.7 Hz), 7.38 (d, 1H, J=8.7 Hz), 7.00-6.96 (m, 4H), 6.40 (dd, 2H, J=1.4 Hz, 17.4 Hz), 6.12 (dd, 2H, J=10.6 Hz, 17.4 Hz), 5.82 (dd, 2H, J=1.4 Hz, 10.6 Hz), 4.18 (t, 4H, J=6.4 Hz), 4.08-4.04 (m, 4H), 1.88-1.81 (m, 4H), 1.76-1.69 (m, 4H), 1.58-1.42 (m, 8H).

Step 2: Synthesis of Compound A

A four-necked reactor equipped with a thermometer was charged with 10.5 g (15.3 mmol) of the intermediate D synthesized in the step 1, 3.0 g (18.3 mmol) of 2-hydrazinobenzothiazole, and 80 ml of THF under a nitrogen stream to prepare a homogeneous solution. After the addition of 18 mg (0.08 mmol) of (±)-10-camphorsulfonic acid to the solution, the mixture was stirred at 25° C. for 3 hours.

Compound A

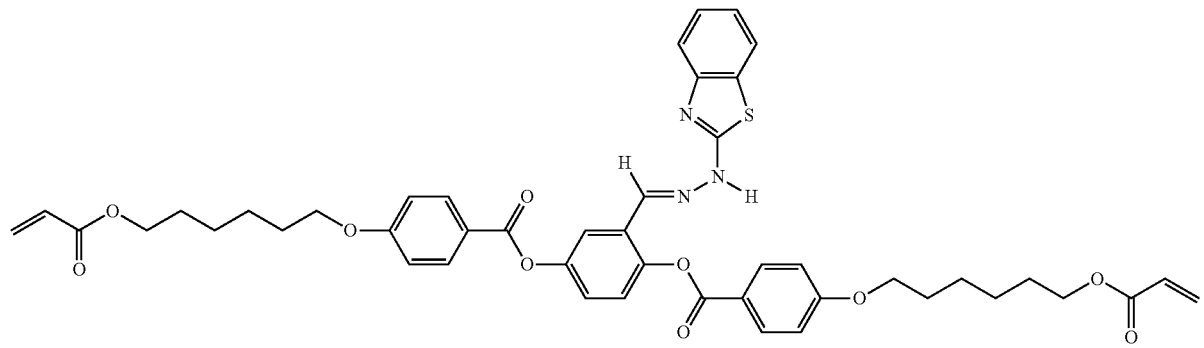

Step 1: Synthesis of Intermediate D

Intermediate D

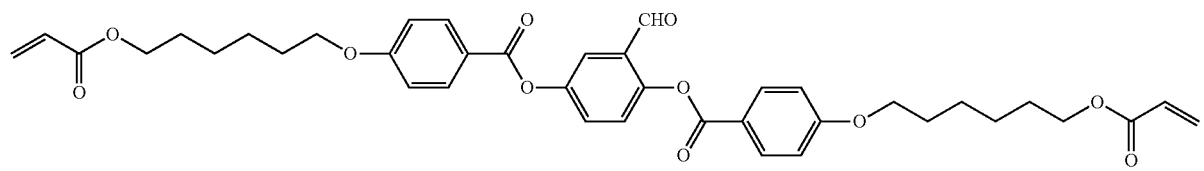

A four-necked reactor equipped with a thermometer was charged with 20 g (144.8 mmol) of 2,5-dihydroxybenzaldehyde, 105.8 g (362.0 mmol) of 4-(6-acryloylhex-1-yloxy) benzoic acid (manufactured by DKSH Japan K.K.), 5.3 g (43.4 mmol) of 4-(dimethylamino)pyridine, and 200 ml of N-methylpyrrolidone under a nitrogen stream to prepare a After completion of the reaction, the reaction mixture was added to 800 ml of 10% sodium bicarbonate water, followed by extraction twice with 100 ml of ethyl acetate. The ethyl acetate layer was collected, and dried over anhydrous sodium sulfate, and sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=8:2) to obtain 8.0 g of a compound A as a light yellow solid (yield: 62.7%).

The structure of the target product was identified by $^1$H-NMR and mass spectroscopy.

$^1$H-NMR (500 MHz, DMSO-$d_6$, TMS, δ ppm): 12.30 (br, 1H), 8.19 (s, 1H), 8.17-8.12 (m, 4H), 7.76 (d, 1H, J=3.0 Hz), 7.68 (d, 1H, J=7.5 Hz), 7.45-7.39 (m, 3H), 7.28 (t, 1H, J=8.0 Hz), 7.18-7.14 (m, 4H), 7.09 (t, 1H, J=8.0 Hz), 6.33 (dd, 2H, J=1.5 Hz, 17.5 Hz), 6.18 (dd, 2H, J=10.5 Hz, 17.5 Hz), 5.944 (dd, 1H, J=1.5 Hz, 10.5 Hz), 5.941 (dd, 1H, J=1.5 Hz, 10.5 Hz), 4.14-4.10 (m, 8H), 1.80-1.75 (m, 4H), 1.69-1.63 (m, 4H), 1.53-1.38 (m, 8H).

LCMS (APCI): calcd for $C_{46}H_{47}N_3O_{10}S$: 833[M$^+$]; Found: 833.

The phase transition temperature was measured as described below using the compounds 1 to 3 obtained in Examples 1 to 3, the compound 1r of Reference Example 1 that was used in Comparative Example 1 ("K35" manufactured by Zeon Corporation), and the compound 2r of Reference Example 2 that was used in Comparative Example 2 ("LC242" manufactured by BASF).

TABLE 1

| | Compound | Phase transition temperature |
|---|---|---|
| Example 1 | Compound 1 | C ⇌ I  (152° C. / 75° C.) |
| Example 2 | Compound 2 | C ⇌ I  (96° C. / 75° C.) |
| Example 3 | Compound 3 | C ⇌ I  (168° C. / 45° C. or less) |
| Reference Example 1 | Compound 1r | C ⇌ N ⇌ I  (80° C. / 40° C. or less; 200° C. or more) |
| Reference Example 2 | Compound 2r | C ⇌ N ⇌ I  (60° C. / 40° C. or less; 123° C. / 122° C.) |

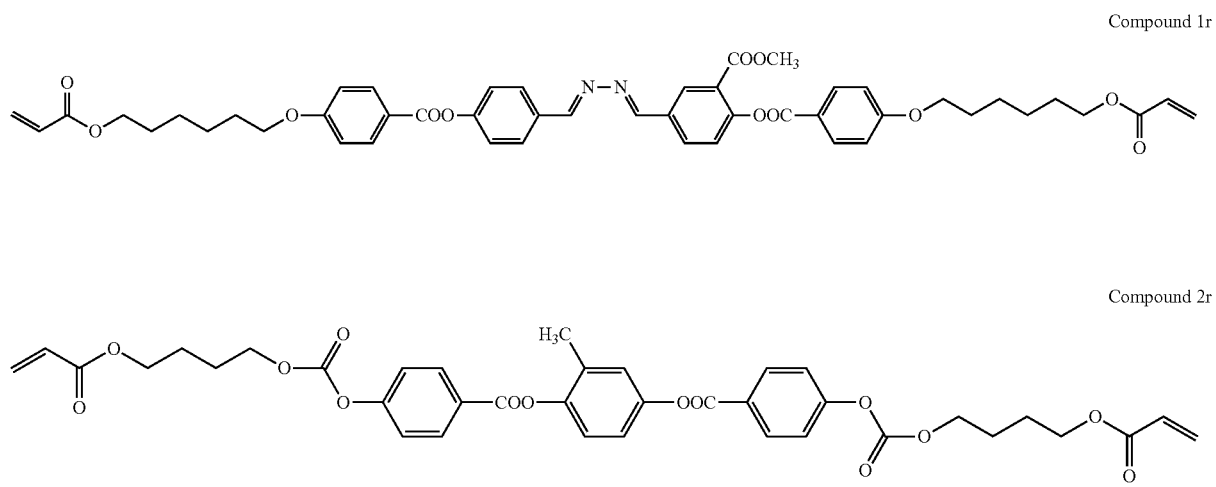

Compound 1r

Compound 2r

Measurement of Phase Transition Temperature 10 mg of each compound (compounds 1 to 3, compound 1r, and compound 2r) was weighed, and placed in a solid state between two glass substrates provided with a polyimide alignment film subjected to a rubbing treatment. The substrates were placed on a hot plate, heated from 40° C. to 200° C., and cooled to 40° C. A change in structure during a change in temperature was observed using a polarizing optical microscope ("ECLIPSE LV100POL" manufactured by Nikon Corporation).

The phase transition temperature measurement results are shown in Table 1. In Table 1, "C" refers to "crystal", "N" refers to "nematic", and "I" refers to "isotropic". The term "crystal" means that the test compound was in a solid phase, the term "nematic" means that the test compound was in a nematic liquid crystal phase, and the term "isotropic" means that the test compound was in an isotropic liquid phase.

Example 4

0.5 g of the compound 1 obtained in Example 1, 2.0 g of the compound A obtained in Synthesis Example 1, 75 mg of Adekaoptomer N-1919 (manufactured by Adeka Corporation (hereinafter the same)) (photoinitiator), and 250 mg of a 1% cyclopentanone solution of KH-40 (manufactured by AGC Seimi Chemical Co., Ltd. (hereinafter the same)) (surfactant) were dissolved in 2.1 g of cyclopentanone and 7.65 g of chloroform. The solution was filtered through a disposable filter having a pore size of 0.45 μm to obtain a polymerizable composition 1.

Example 5

0.34 g of the compound 2 obtained in Example 2, 0.66 g of the compound A obtained in Synthesis Example 1, 30 mg of Adekaoptomer N-1919 (photoinitiator), and 100 mg of a 1% cyclopentanone solution of KH-40 (surfactant) were dissolved in 2.2 g of cyclopentanone. The solution was filtered through a disposable filter having a pore size of 0.45 μm to obtain a polymerizable composition 2.

Example 6

0.5 g of the compound 3 obtained in Example 3, 0.5 g of the compound A obtained in Synthesis Example 1, 30 mg of Adekaoptomer N-1919 (photoinitiator), and 100 mg of a 1% cyclopentanone solution of KH-40 (surfactant) were dissolved in 3.85 g of chloroform. The solution was filtered through a disposable filter having a pore size of 0.45 μm to obtain a polymerizable composition 3.

Example 7

0.34 g of the compound 3 obtained in Example 3, 0.66 g of the compound A obtained in Synthesis Example 1, 30 mg of Adekaoptomer N-1919 (photoinitiator), and 100 mg of a 1% cyclopentanone solution of KH-40 (surfactant) were dissolved in 3.85 g of chloroform. The solution was filtered through a disposable filter having a pore size of 0.45 μm to obtain a polymerizable composition 4.

Comparative Examples 1 and 2

1.0 g of the compound 1r or 2r, 30 mg of Adekaoptomer N-1919 (photoinitiator), and 100 mg of a 1% cyclopentanone solution of KH-40 (surfactant) were dissolved in 2.3 g of cyclopentanone. The solution was filtered through a disposable filter having a pore size of 0.45 μm to obtain a polymerizable composition 1r or 2r, respectively.

Measurement of Retardation and Evaluation of Wavelength Dispersion (i) Formation of Liquid Crystal Layer Using Polymerizable Composition Each polymerizable composition (polymerizable compositions 1 to 4, 1r, and 2r) was applied to a transparent glass substrate provided with a polyimide alignment film subjected to a rubbing treatment (manufactured by E.H.C. Co., Ltd.) using a #4 wire bar. The resulting film was dried for 30 seconds at the temperature shown in Table 2, and subjected to an alignment treatment for 1 minute at the temperature shown in Table 2 to form a liquid crystal layer. Ultraviolet rays were applied to the liquid crystal layer at a dose of 2000 mJ/cm² to effect polymerization to prepare a wavelength dispersion measurement sample.

(ii) Measurement of Retardation

The retardation between 400 nm and 800 nm was measured using the sample utilizing an ellipsometer ("M2000U" manufactured by J. A. Woollam).

(iii) Evaluation of Wavelength Dispersion

The wavelength dispersion was evaluated from the values α and β that were calculated by the following expressions using the measured retardation.

$\alpha$=(retardation at 449.9 nm)/(retardation at 548.5 nm)
$\beta$=(retardation at 650.2 nm)/(retardation at 548.5 nm)

The value α is smaller than 1, and the value β is larger than 1 when ideal wideband wavelength dispersion (reverse wavelength dispersion) is achieved. The values α and β are almost identical when flat wavelength dispersion is achieved. The value α is larger than 1, and the value β is smaller than 1 when normal dispersion is achieved.

Table 2 shows the thickness (μm) of the liquid crystal polymer films obtained by polymerizing the polymerizable compositions, the retardation (Re) at a wavelength of 548.5 nm, and the values α and β.

Note that "Ratio (%)" in Table 2 refers to the ratio (mass %) of the amount of the polymerizable compound.

TABLE 2

| | Polymerizable composition | Polymerizable compound 1 | | Polymerizable compound 2 | | Drying temperature (° C.) | Alignment temperature (° C.) | Thickness (μm) | Re (548.5 nm) | α | β |
| --- | --- | --- | --- | --- | --- | --- | --- | --- | --- | --- | --- |
| | | Compound | Ratio (%) | Compound | Ratio (%) | | | | | | |
| Example 4 | 1 | 1 | 20 | A | 80 | 160 | 23 | 1.435 | 100.57 | 0.303 | 1.063 |
| Example 5 | 2 | 2 | 34 | A | 66 | 120 | 23 | 1.358 | 124.37 | 0.949 | 1.005 |
| Example 6 | 3 | 3 | 50 | A | 50 | 140 | 23 | 1.874 | 93.01 | 0.158 | 1.100 |
| Example 7 | 4 | 3 | 34 | A | 66 | 140 | 23 | 1.870 | 124.50 | 0.270 | 1.072 |
| Comparative Example 1 | 1r | 1r | 100 | — | — | 90 | 23 | 1.509 | 355.97 | 1.193 | 0.918 |
| Comparative Example 2 | 2r | 2r | 100 | — | — | 80 | 23 | 1.479 | 222.9 | 1.086 | 0.970 |

As shown in Table 2, the polymers obtained in Examples 4 to 7 according to the invention had a wavelength dispersion in which the value α was smaller than 1, and the value β was larger than 1.

The invention claimed is:

1. A polymerizable compound represented by a formula (I),

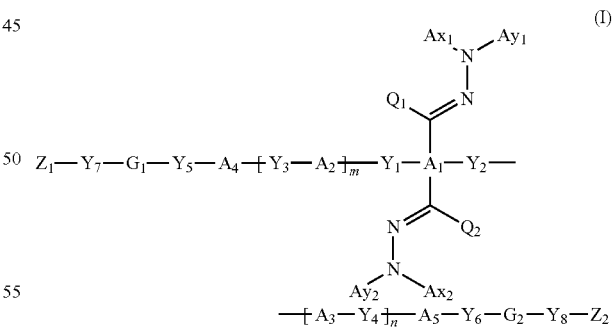

wherein $Y^1$ to $Y^8$ are independently a chemical single bond, —O—, —S—, —O—C(=O)—, —C(=O)—O—, —O—C(=O)—O—, —NR¹—C(=O)—, —C(=O)—NR¹—, —O—C(=O)—NR¹—, —NR¹—C(=O)—O—, —NR¹—C(=O)—NR¹—, —O—NR¹—, or —NR¹—O—, R¹ is a hydrogen atom or an alkyl group having 1 to 6 carbon atoms, $G^1$ and $G^2$ are independently a substituted or unsubstituted divalent aliphatic group having 1 to 20 carbon atoms that optionally includes —O—, —S—, —O—C(=O)—, —C(=O)—O—, —O—C(=O)—O—, —NR²—C(=O)—, —C(=O)—NR²—, —NR²—, or —C(=O)—, provided that a case where the aliphatic group includes two or more contiguous —O— or —S— is excluded, R² is a hydrogen atom or an alkyl group having 1 to 6 carbon atoms, $Z^1$ and $Z^2$ are independently an alkenyl group having 2 to 10 carbon atoms that is substituted with a halogen atom, or unsubstituted, $A^1$ is a substituted or unsubstituted tetravalent aromatic group having 4 to 30 carbon atoms, $A^2$ and $A^3$ are independently a substituted or unsubstituted divalent alicyclic hydrocarbon group having 3 to 30 carbon atoms, $A^4$ and $A^5$ are independently a substituted or unsubstituted divalent aromatic group having 4 to 30 carbon atoms, $A^{x1}$ and $A^{x2}$ are independently an organic group having 2 to 30 carbon atoms that includes at least one ring selected from a group consisting of a hydrocarbon ring and a heterocyclic ring, $A^{y1}$ and $A^{y2}$ are independently a hydrogen atom, a substituted or unsubstituted alkyl group having 1 to 6 carbon atoms, or an organic group having 2 to 30 carbon atoms that includes at least one ring selected from a group consisting of a hydrocarbon ring and a heterocyclic ring, provided that the ring included in $A^{x1}$, the ring included in $A^{x2}$, the ring optionally included in $A^{y1}$, and the ring optionally included in $A^{y2}$ are either substituted or unsubstituted, $A^{x1}$ and $A^{y1}$ are optionally bonded to each other to form a ring, and $A^{x2}$ and $A^{y2}$ are optionally bonded to each other to form a ring, $Q^1$ and $Q^2$ are independently a hydrogen atom, or a substituted or unsubstituted alkyl group having 1 to 6 carbon atoms, and m and n are independently 0 or 1.

2. The polymerizable compound according to claim 1, wherein the ring included in $A^{y1}$, the ring included in $A^{x2}$, the ring optionally included in $A^{y1}$, and the ring optionally included in $A^{y2}$ are an aromatic ring.

3. The polymerizable compound according to claim 1, wherein a total number of aromatic ring π electrons included in $A^{x1}$ and $A^{y1}$ is 24 or less, and a total number of aromatic ring π electrons included in $A^{x2}$ and $A^{y2}$ is 24 or less.

4. The polymerizable compound according to claim 1, wherein the ring that is optionally formed by $A^{x1}$ and $A^{y1}$, and the ring that is optionally formed by $A^{x2}$ and $A^{y2}$, are a nitrogen-containing heterocyclic ring represented by a formula (II),

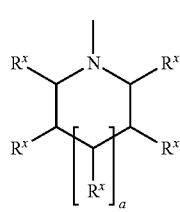

(II)

wherein $R^x$ are a hydrogen atom, a halogen atom, an alkyl group having 1 to 6 carbon atoms, a cyano group, a nitro group, an alkylsulfinyl group having 1 to 6 carbon atoms, an alkylsulfonyl group having 1 to 6 carbon atoms, a fluoroalkyl group having 1 to 6 carbon atoms, or an alkoxy group having 1 to 6 carbon atoms, provided that are either identical or different, an arbitrary C—R" linkage that forms the ring is optionally substituted with N—R³ (R³ is a hydrogen atom or an alkyl group having 1 to 6 carbon atoms) or —O—, and the ring optionally includes an unsaturated bond, a is an integer from 0 to 2, and "-" is a bonding position.

5. The polymerizable compound according to claim 1, wherein $A^1$ is a substituted or unsubstituted tetravalent benzene ring group, or a substituted or unsubstituted tetravalent naphthalene ring group, and $A^4$ and $A^5$ are independently a substituted or unsubstituted phenylene group, or a substituted or unsubstituted naphthylene group.

6. The polymerizable compound according to claim 1, wherein $Y^1$ to $Y^8$ are independently a chemical single bond, —O—, —O—C(=O)—, —C(=O)—O—, or —O—C(=O)—O—.

7. The polymerizable compound according to claim 1, wherein $Z^1$ and $Z^2$ are independently $CH_2$=CH—, $CH_2$=C(CH_3)—, or $CH_2$=C(Cl)—.

8. The polymerizable compound according to claim 1, wherein $G^1$ and $G^2$ are independently a substituted or unsubstituted divalent aliphatic group having 1 to 12 carbon atoms that optionally includes —O—, —O—C(=O)—, —C(=O)—O—, or —C(=O)—, provided that a case where the aliphatic group includes two or more contiguous —O— is excluded.

9. The polymerizable compound according to claim 1, wherein $Y^1$ to $Y^8$ are independently a chemical single bond, —O—, —O—C(=O)—, —C(=O)—O—, or —O—C(=O)—O—, $Z^1$ and $Z^2$ are independently $CH_2$=CH—, $CH_2$=C(CH_3)—, or $CH_2$=C(Cl)—, and $G^1$ and $G^2$ are independently a divalent alkylene group having 1 to 12 carbon atoms.

10. A polymerizable composition comprising at least one type of the polymerizable compound according to claim 1.

11. A polymerizable composition comprising the polymerizable compound according to claim 1, and an initiator.

12. A polymer obtained by polymerizing the polymerizable compound according to claim 1.

13. The polymer according to claim 12, the polymer being a liquid crystalline polymer.

14. An optically anisotropic article comprising the polymer according to claim 13.

15. The polymerizable compound according to claim 2, wherein $Y^1$ to $Y^8$ are independently a chemical single bond, —O—, —O—C(=O)—, —C(=O)—O—, or —O—C(=O)—O—.

16. The polymerizable compound according to claim 3, wherein $Y^1$ to $Y^8$ are independently a chemical single bond, —O—, —O—C(=O)—, —C(=O)—O—, or —O—C(=O)—O—.

17. The polymerizable compound according to claim 4, wherein $Y^1$ to $Y^8$ are independently a chemical single bond, —O—, —O—C(=O)—, —C(=O)—O—, or —O—C(=O)—O—.

18. The polymerizable compound according to claim 5, wherein $Y^1$ to $Y^8$ are independently a chemical single bond, —O—, —O—C(=O)—, —C(=O)—O—, or —O—C(=O)—O—.

19. A polymerizable composition comprising at least one type of the polymerizable compound according to claim 2.

20. A polymer obtained by polymerizing the polymerizable composition according to claim 10.

* * * * *